United States Patent
Shibai et al.

(10) Patent No.: US 10,968,292 B2
(45) Date of Patent: Apr. 6, 2021

(54) SYNTHETIC POLYMER FILM WHOSE SURFACE HAS MICROBICIDAL ACTIVITY, PHOTOCURABLE RESIN COMPOSITION, MANUFACTURING METHOD OF SYNTHETIC POLYMER FILM, AND STERILIZATION METHOD WITH USE OF SURFACE OF SYNTHETIC POLYMER FILM

(71) Applicant: SHARP KABUSHIKI KAISHA, Sakai (JP)

(72) Inventors: Yasuhiro Shibai, Sakai (JP); Miho Yamada, Sakai (JP); Ken Atsumo, Sakai (JP); Kiyoshi Minoura, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 0 days.

(21) Appl. No.: 16/141,883

(22) Filed: Sep. 25, 2018

(65) Prior Publication Data

US 2019/0092883 A1 Mar. 28, 2019

(30) Foreign Application Priority Data

Sep. 26, 2017 (JP) .............................. JP2017-185204
Nov. 27, 2017 (JP) .............................. JP2017-226887

(51) Int. Cl.
*C08J 5/18* (2006.01)
*C08F 22/10* (2006.01)
(Continued)

(52) U.S. Cl.
CPC .......... *C08F 22/1006* (2020.02); *A01N 25/10* (2013.01); *A01N 37/04* (2013.01);
(Continued)

(58) Field of Classification Search
CPC ......... B32B 3/26–30; Y10T 428/24355; Y10T 428/24364; Y10T 428/24479–2462;
(Continued)

(56) References Cited

U.S. PATENT DOCUMENTS 9,781,924 B2  10/2017  Yamada et al.
9,781,925 B2  10/2017  Yamada et al.
(Continued)

FOREIGN PATENT DOCUMENTS

CA        2323719 A1    4/2001
CN     201329050 Y   10/2009
(Continued)

OTHER PUBLICATIONS

Machine translation of JP 2016/104545 A, obtained from the JPO (Year: 2019).*
(Continued)

*Primary Examiner* — Z. Jim Yang
(74) *Attorney, Agent, or Firm* — ScienBiziP, P.C.

(57) ABSTRACT

A synthetic polymer film is a synthetic polymer film whose surface has a plurality of raised or recessed portions. The synthetic polymer film has a crosslink structure, and the crosslink structure does not contain any nitrogen element that is a constituent of a urethane bond. The synthetic polymer film contains an organic carboxylic acid, and an amount of water required for dissolving 1 g of the organic carboxylic acid is equal to or greater than 10 mL and less than 10000 mL. At the lapse of 5 minutes since placing a 200 µL drop of water on the surface of the synthetic polymer film, a pH of an aqueous solution is not more than 5, and an area equivalent circle diameter of the aqueous solution is not less than 20 mm. A synthetic polymer film whose surface has a microbicidal activity can be produced using a photocurable resin composition which contains an organic carboxylic acid
(Continued)

or a photoacid generator which generates the organic carboxylic acid.

9 Claims, 8 Drawing Sheets

(51) Int. Cl.
| | | |
|---|---|---|
| *C08K 5/09* | (2006.01) | |
| *C08K 5/092* | (2006.01) | |
| *C08K 5/521* | (2006.01) | |
| *A61L 2/23* | (2006.01) | |
| *A01N 57/14* | (2006.01) | |
| *A01N 25/10* | (2006.01) | |
| *C02F 1/50* | (2006.01) | |
| *A01N 37/04* | (2006.01) | |
| *A01N 37/10* | (2006.01) | |
| *C08F 2/48* | (2006.01) | |
| *C08F 220/28* | (2006.01) | |

(52) U.S. Cl.
CPC ............. *A01N 37/10* (2013.01); *A01N 57/14* (2013.01); *A61L 2/23* (2013.01); *C02F 1/50* (2013.01); *C08F 2/48* (2013.01); *C08J 5/18* (2013.01); *C08K 5/09* (2013.01); *C08K 5/092* (2013.01); *C08K 5/521* (2013.01); *C02F 2303/04* (2013.01); *C08F 220/286* (2020.02); *C08F 2810/20* (2013.01); *C08J 2335/02* (2013.01); *Y10T 428/24355* (2015.01)

(58) Field of Classification Search
CPC ........ A01N 25/10; A01N 37/10; B08B 17/06; B08B 17/065; C08F 122/105; C08F 222/1006; C08F 2222/1066; C08F 2222/108; G02B 1/118
See application file for complete search history.

(56) References Cited

U.S. PATENT DOCUMENTS

| | | | |
|---|---|---|---|
| 9,781,926 B2 | 10/2017 | Yamada et al. | |
| 10,136,638 B2 | 11/2018 | Yamada et al. | |
| 2003/0164326 A1 | 9/2003 | Eberl et al. | |
| 2003/0205475 A1 | 11/2003 | Sawitowski | |
| 2005/0163854 A1* | 7/2005 | Hartman | A01N 59/00 424/486 |
| 2007/0159698 A1 | 7/2007 | Taguchi et al. | |
| 2008/0145390 A1* | 6/2008 | Taylor | A01N 31/02 424/405 |
| 2009/0252825 A1 | 10/2009 | Taguchi et al. | |
| 2010/0009137 A1 | 1/2010 | Kodama | |
| 2010/0203161 A1 | 8/2010 | Gehri et al. | |
| 2010/0234323 A1 | 9/2010 | Holzl et al. | |
| 2010/0263793 A1* | 10/2010 | Ylitalo | A01N 25/34 156/714 |
| 2011/0038910 A1 | 2/2011 | Faucher et al. | |
| 2011/0235181 A1 | 9/2011 | Hayashibe et al. | |
| 2011/0281068 A1 | 11/2011 | David et al. | |
| 2012/0218639 A1* | 8/2012 | Minoura | B29C 33/56 359/601 |
| 2012/0318772 A1 | 12/2012 | Minoura et al. | |
| 2013/0057958 A1 | 3/2013 | Minoura et al. | |
| 2013/0260096 A1* | 10/2013 | Shiki | C23C 18/1216 428/142 |
| 2013/0344290 A1 | 12/2013 | Yu et al. | |
| 2014/0004304 A1 | 1/2014 | Yu et al. | |
| 2014/0077418 A1 | 3/2014 | Otani et al. | |
| 2015/0009571 A1* | 1/2015 | Chin | C25D 1/10 359/601 |
| 2015/0140154 A1* | 5/2015 | Isurugi | C25D 11/12 425/177 |
| 2015/0168610 A1* | 6/2015 | Fukui | B29C 33/424 428/141 |
| 2015/0273755 A1 | 10/2015 | Yee et al. | |
| 2016/0113274 A1 | 4/2016 | Yamada et al. | |
| 2016/0194778 A1* | 7/2016 | Shakagoori | B29C 59/046 359/601 |
| 2016/0212989 A1 | 7/2016 | Juodkazis et al. | |
| 2017/0258081 A1 | 9/2017 | Yamada et al. | |
| 2017/0285468 A1* | 10/2017 | Kitagawa | B41M 7/0081 |
| 2018/0036995 A1 | 2/2018 | Okazaki et al. | |
| 2018/0134859 A1 | 5/2018 | Yamada et al. | |
| 2018/0163056 A1* | 6/2018 | Okazaki | C08J 7/04 |
| 2019/0161636 A1* | 5/2019 | Gokhale | A01N 25/10 |

FOREIGN PATENT DOCUMENTS

| | | |
|---|---|---|
| DE | 19950452 A1 | 4/2001 |
| JP | H08-024843 A | 1/1996 |
| JP | H08-300549 A | 11/1996 |
| JP | H11-010724 A | 1/1999 |
| JP | 2001-219464 A | 8/2001 |
| JP | 2001-310412 A | 11/2001 |
| JP | 2002-012257 A | 1/2002 |
| JP | 2005-055114 A | 3/2005 |
| JP | 2008-197217 A | 8/2008 |
| JP | 4265729 B | 2/2009 |
| JP | 2009-166502 A | 7/2009 |
| JP | 2010-000719 A | 1/2010 |
| JP | 2010-079200 A | 4/2010 |
| JP | 2012-078438 A | 4/2012 |
| JP | 2012-514239 A | 6/2012 |
| JP | 2012-208169 A | 10/2012 |
| JP | 2013-033287 A | 2/2013 |
| JP | 2013-078573 A | 5/2013 |
| JP | 2013-208817 A | 10/2013 |
| JP | 2014-005341 A | 1/2014 |
| JP | 2014-029391 A | 2/2014 |
| JP | 2014-066975 A | 4/2014 |
| JP | 2014-509967 A | 4/2014 |
| JP | 2014-511779 A | 5/2014 |
| JP | 2014-202955 A | 10/2014 |
| JP | 2015-024549 A | 2/2015 |
| JP | 2015-152659 | 8/2015 |
| JP | 5788128 B1 | 9/2015 |
| JP | 2016-026546 A | 2/2016 |
| JP | 2016-093939 A | 5/2016 |
| JP | 2016-104545 A | 6/2016 |
| JP | 2016-210164 A | 12/2016 |
| JP | 2017-048132 A | 3/2017 |
| WO | 2007/097454 A1 | 8/2007 |
| WO | 2011/019834 A1 | 2/2011 |
| WO | 2011/052652 A1 | 5/2011 |
| WO | 2011/125486 A1 | 10/2011 |
| WO | 2011/148721 A1 | 12/2011 |
| WO | 2012/161315 A1 | 11/2012 |
| WO | 2013/183576 A1 | 12/2013 |
| WO | 2013/191092 A1 | 12/2013 |
| WO | 2014/021376 A1 | 2/2014 |
| WO | 2014/171365 A1 | 10/2014 |
| WO | 2015/031956 A1 | 3/2015 |
| WO | 2015/163018 A1 | 10/2015 |
| WO | 20161080245 A1 | 5/2016 |
| WO | 2016/084745 A1 | 6/2016 |
| WO | 2016/143778 A1 | 9/2016 |
| WO | 2016/175170 A1 | 11/2016 |
| WO | 2016/182444 A1 | 11/2016 |
| WO | 2016/208540 A1 | 12/2016 |
| WO | 2017/090661 A1 | 6/2017 |
| WO | 2017/168893 A1 | 10/2017 |
| WO | 2018/154843 A1 | 8/2018 |

OTHER PUBLICATIONS

Co-pending letter regarding related co-pending U.S. Appl. No. 14/771,833, filed Sep 1, 2015 et al.

Non-Final Rejection dated Nov. 24, 2017 for U.S. Appl. No. 14/897,252.

(56) References Cited

OTHER PUBLICATIONS

Non-Final Rejection dated Dec. 11, 2017 for U.S. Appl. No. 15/592,922.
Non-Final Office Action dated Jan. 24, 2018 for U.S. Appl. No. 15/126,078.
Espeel Pieter, et al. "One-pot, additive-free preparation of functionalized polyurethanes via amine—thiol—ene conjugation", Polymer Chemistry, 2013, 4(8):2449-2456.
Pogodin Sergey, et al. "Biophysical model of bacterial cell interactions with nanopatterned cicada wing surfaces", Biophysical Journal, 2013, 104(4):835-840.
Compound Summary for CID 3086063, Tecoflex from PubChem, accessed Jan. 17, 2018.
Final Office Action dated Apr. 13, 2018 for U.S. Appl. No. 14/897,252.
Final Office Action dated Jun. 14, 2018 for U.S. Appl. No. 15/592,922.
Non-Final Office Action dated Jul. 13, 2018 for U.S. Appl. No. 15/784,771.
Elena P. Ivanova, et al, "Bactericidal activity of black silicon", Nature Communications, Jun. 7, 2013, Article No. 2838 (2013), DOI: 10.1038/ncomms3838.
Alexander K. Epstein, et al, "Liquid-infused structured surfaces with exceptional anti-biofouling performance", Proc Natl Acad Sci U S A. Aug. 14, 2012; 109(33): 13182-13187. doi: 10.1073/pnas.1201973109.
Elena P. Ivanova, et al, Natural Bactericidal Surfaces: Mechanical Rupture of Pseudomonas aeruginosa Cells by cicada Wings,Small. Aug. 20, 2012;8(16):2489-94. doi: 10.1002/smll.201200528.
Hang Yao, Thomas J. Webster, Matthew Hedrick,"Decreased bacteria density on nanostructured polyurethane", J Biomed Mater Res Part A 2014:102A:1823-1828.
Cleaning Guide—How to Clean Surface,http://www.goodhousekeeping.com/home/cleaning/tips/a18875/how-to-clean, Sep 7, 2011.
MIT's anti-microbial 'paint 'kills flu,bacteria,Anne Trafton, Nov. 30, 2006,http://chemistry.mit.edu/mits-anti-microbial-paint-kills-flu-bacteria.
Rosa M. Raybaudi-Massilia et al. "Control of Pathogenic and Spoilage Microorganisms in Fresh-cut Fruits and Fruit Juices by Traditional and Alternative Natural Antimicrobials", Comprehensive Reviews in Food Science and Food Safety, 2009, 8:157-180.
Jafar Hasan et al., "Antibacterial surfaces: the quest for a new generation of biomaterials", Trends in Biotechnology, vol. 31, Issue 5, May 2013, pp. 295-304.
Alexander K. Epstein et al., "Liquid-infused structured surfaces with exceptional anti-biofouling performance", PNAS, vol. 109, No. 33, Aug. 14, 2012, pp. 13182-13187.

* cited by examiner

5μm

5μm

SYNTHETIC POLYMER FILM WHOSE SURFACE HAS MICROBICIDAL ACTIVITY, PHOTOCURABLE RESIN COMPOSITION, MANUFACTURING METHOD OF SYNTHETIC POLYMER FILM, AND STERILIZATION METHOD WITH USE OF SURFACE OF SYNTHETIC POLYMER FILM

BACKGROUND

1. Technical Field

The present invention relates to a synthetic polymer film whose surface has a microbicidal activity, a photocurable resin composition for use in formation of the synthetic polymer film, a manufacturing method of the synthetic polymer film, and a sterilization method with the use of the surface of the synthetic polymer film.

2. Description of the Related Art

Recently, it was reported that surficial nanostructures of black silicon, wings of cicadas and dragonflies have a bactericidal activity (Ivanova, E. P. et al., "Bactericidal activity of black silicon", Nat. Commun. 4:2838 doi: 10.1038/ncomms3838 (2013)). Reportedly, the physical structure of the nanopillars that black silicon and wings of cicadas and dragonflies have produces a bactericidal activity.

According to Ivanova, E. P. et al., black silicon has the strongest bactericidal activity on Gram-negative bacteria, while wings of dragonflies have a weaker bactericidal activity, and wings of cicadas have a still weaker bactericidal activity. Black silicon has 500 nm tall nanopillars. Wings of cicadas and dragonflies have 240 nm tall nanopillars. The static contact angle (hereinafter, also simply referred to as "contact angle") of the black silicon surface with respect to water is 80°, while the contact angles of the surface of wings of dragonflies and cicadas with respect to water are 153° and 159°, respectively. It is estimated that black silicon is mainly made of silicon, and wings of dragonflies and cicadas are made of chitin. According to Ivanova, E. P. et al., the composition of the surface of black silicon is generally a silicon oxide, and the composition of the surface of wings of dragonflies and cicadas is generally a lipid.

SUMMARY

The mechanism of killing bacteria by nanopillars is not clear from the results described in Ivanova, E. P. et al. It is also not clear whether the reason why black silicon has a stronger bactericidal activity than wings of dragonflies and cicadas resides in the difference in height or shape of nanopillars, in the difference in surface free energy (which can be evaluated by the contact angle), in the materials that constitute nanopillars, or in the chemical properties of the surface.

The bactericidal activity of black silicon is difficult to utilize because black silicon is poor in mass productivity and is hard but brittle so that the shapability is poor.

A major object of the present invention is to provide a synthetic polymer film whose surface has a microbicidal activity, a photocurable resin composition for use in formation of the synthetic polymer film, a synthetic polymer film production method, and a sterilization method with the use of the surface of the synthetic polymer film.

A synthetic polymer film of an embodiment of the present invention is a synthetic polymer film whose surface has a plurality of raised or recessed portions, wherein the synthetic polymer film has a crosslink structure, and the crosslink structure does not contain any nitrogen element that is a constituent of a urethane bond, the synthetic polymer film contains an organic carboxylic acid, and an amount of water required for dissolving 1 g of the organic carboxylic acid is equal to or greater than 10 mL and less than 10000 mL, and at the lapse of 5 minutes since placing a 200 µL drop of water on the surface of the synthetic polymer film, a pH of an aqueous solution is not more than 5, and an area equivalent circle diameter of the aqueous solution is not less than 20 mm.

As for the solubility of the organic carboxylic acid in water, the amount of water required for dissolving 1 g of the organic carboxylic acid is preferably not less than 100 mL, more preferably not less than 200 mL, and is preferably less than 2000 mL.

In one embodiment, when viewed in a normal direction of the synthetic polymer film, a two-dimensional size of the plurality of raised or recessed portions is in the range of more than 20 nm and not more than 1 µm.

In one embodiment, when viewed in the normal direction of the synthetic polymer film, the two-dimensional size of the plurality of raised or recessed portions is less than 500 nm.

In one embodiment, when viewed in the normal direction of the synthetic polymer film, the two-dimensional size of the plurality of raised or recessed portions is not less than 500 nm.

In one embodiment, the synthetic polymer film further contains an acid stronger than the organic carboxylic acid. The acid stronger than the organic carboxylic acid is, for example, phosphoric acid or sulfonic acid.

In one embodiment, the organic carboxylic acid is 2,4,6-trimethylbenzoic acid, suberic acid or sebacic acid. The amount of water required for dissolving 1 g of these organic carboxylic acids is equal to or greater than 200 mL and less than 2000 mL.

In one embodiment, the synthetic polymer film is made of a photocurable resin, and the organic carboxylic acid is generated by photodecomposition of a photopolymerization initiator contained in the photocurable resin.

In one embodiment, the photopolymerization initiator contains bis(2,4,6-trimethylbenzoyl)-phenylphosphine oxide.

In one embodiment, the photopolymerization initiator further contains diphenyl (2,4,6-trimethylbenzoyl) phosphine oxide.

In one embodiment, the crosslink structure contains an ethylene oxide unit.

A liquid sterilization method of an embodiment of the present invention is a method for sterilizing a liquid including water by bringing the liquid into contact with the surface of the synthetic polymer film as set forth in any of the foregoing paragraphs.

A photocurable resin composition of an embodiment of the present invention is a photocurable resin composition for use in production of a synthetic polymer film whose surface has a microbicidal activity, including: a photocurable resin; and an organic carboxylic acid or a photoacid generator which generates the organic carboxylic acid, wherein an amount of water required for dissolving 1 g of the organic carboxylic acid is equal to or greater than 10 mL and less than 10000 mL.

In one embodiment, the photocurable resin is radically polymerizable. In one embodiment, the photocurable resin is an acrylic resin. In one embodiment, the photocurable resin is a UV-curable resin.

A method for producing a synthetic polymer film whose surface has a microbicidal activity according to an embodiment of the present invention includes a step of mixing water in the photocurable resin composition as set forth in any of the foregoing paragraphs and thereafter irradiating the resultant photocurable resin composition with light. The amount of the water with respect to the entirety of the photocurable resin composition is equal to or greater than 1 mass % and not more than 10 mass %.

According to an embodiment of the present invention, a synthetic polymer film whose surface has a microbicidal activity, a photocurable resin composition for use in formation of the synthetic polymer film, a synthetic polymer film production method, and a sterilization method with the use of the surface of the synthetic polymer film are provided.

DETAILED DESCRIPTION

Hereinafter, a synthetic polymer film whose surface has a microbicidal effect and a sterilization method with the use of the surface of the synthetic polymer film according to embodiments of the present invention are described with reference to the drawings.

In this specification, the following terms are used.

"Sterilization" (or "microbicidal") means reducing the number of proliferative microorganisms contained in an object, such as solid or liquid, or a limited space, by an effective number.

"Microorganism" includes viruses, bacteria, and fungi.

"Antimicrobial" generally includes suppressing and preventing multiplication of microorganisms and includes suppressing dinginess and slime which are attributed to microorganisms.

The present applicant conceived a method for producing an antireflection film (an antireflection surface) which has a moth-eye structure with the use of an anodized porous alumina layer. Using the anodized porous alumina layer enables manufacture of a mold which has an inverted moth-eye structure with high mass-productivity.

The present inventors developed the above-described technology and arrived at a synthetic polymer film whose surface has a microbicidal effect (see, for example, WO 2015/163018, WO 2016/080245 and WO 2016/208540). The entire disclosures of WO 2015/163018, WO 2016/080245 and WO 2016/208540 are incorporated by reference in this specification.

The configuration of a synthetic polymer film according to an embodiment of the present invention is described with reference to FIG. 1A and FIG. 1B.

Figure 1A:
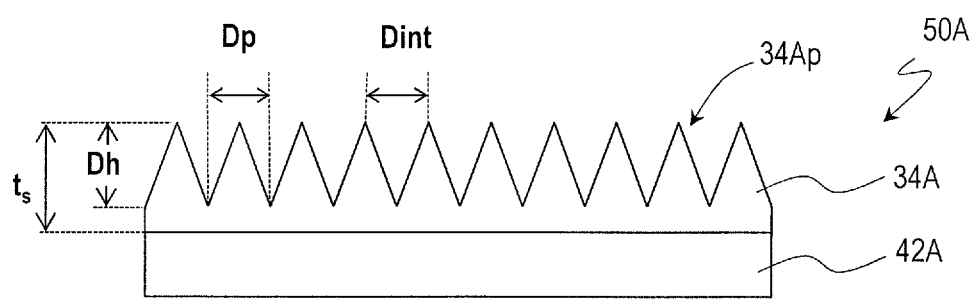
FIG. 1A and FIG. 1B are schematic cross-sectional views of synthetic polymer films 34A and 34B, respectively, according to embodiments of the present invention.
Figure 1B:
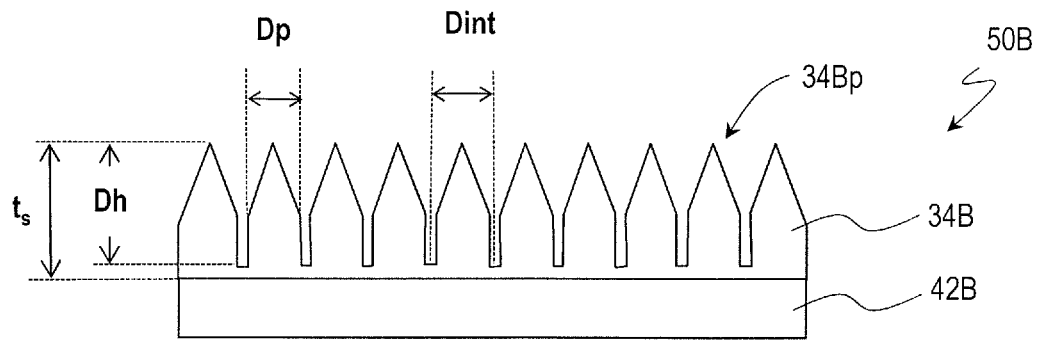

FIG. 1A and FIG. 1B respectively show schematic cross-sectional views of synthetic polymer films 34A and 34B according to embodiments of the present invention. The synthetic polymer films 34A and 34B described herein as examples are formed on base films 42A and 42B, respectively, although the present invention is not limited to these examples. The synthetic polymer films 34A and 34B can be directly formed on a surface of an arbitrary object.

A film 50A shown in FIG. 1A includes a base film 42A and a synthetic polymer film 34A provided on the base film 42A. The synthetic polymer film 34A has a plurality of raised portions 34Ap over its surface. The plurality of raised portions 34Ap constitute a moth-eye structure. When viewed in a normal direction of the synthetic polymer film 34A, the two-dimensional size of the raised portions 34Ap, $D_p$, is in the range of more than 20 nm and less than 500 nm. Here, the "two-dimensional size" of the raised portions 34Ap refers to the diameter of a circle equivalent to the area of the raised portions 34Ap when viewed in a normal direction of the surface. When the raised portions 34Ap have a conical shape, for example, the two-dimensional size of the raised portions 34Ap is equivalent to the diameter of the base of the cone. The typical adjoining distance of the raised portions 34Ap, $D_{int}$, is more than 20 nm and not more than 1000 nm. When the raised portions 34Ap are densely arranged so that there is no gap between adjoining raised portions 34Ap (e.g., the bases of the cones partially overlap each other) as shown in FIG. 1A, the two-dimensional size of the raised portions 34Ap, $D_p$, is equal to the adjoining distance $D_{int}$. The typical height of the raised portions 34Ap, $D_h$, is not less than 50 nm and less than 500 nm. As will be described later, a microbicidal activity is exhibited even when the height $D_h$ of the raised portions 34Ap is not more than 150 nm. The thickness of the synthetic polymer film 34A, $t_s$, is not particularly limited but only needs to be greater than the height $D_h$ of the raised portions 34Ap.

The synthetic polymer film 34A shown in FIG. 1A has the same moth-eye structure as the antireflection films disclosed in Japanese Patent No. 4265729, Japanese Laid-Open Patent Publication No. 2009-166502, WO 2011/125486 and WO 2013/183576. From the viewpoint of producing an antireflection function, it is preferred that the surface has no flat portion, and the raised portions 34Ap are densely arranged over the surface. Further, the raised portions 34Ap preferably has a such shape that the cross-sectional area (a cross section parallel to a plane which is orthogonal to an incoming light ray, e.g., a cross section parallel to the surface of the base film 42A) increases from the air side to the base film 42A side, e.g., a conical shape. From the viewpoint of suppressing interference of light, it is preferred that the raised portions 34Ap are arranged without regularity, preferably randomly. However, these features are unnecessary when only the microbicidal activity of the synthetic polymer film 34A is pursued. For example, the raised portions 34Ap do not need to be densely arranged. The raised portions 34Ap may be regularly arranged. Note that, however, the shape and arrangement of the raised portions 34Ap are preferably selected such that the raised portions 34Ap effectively act on microorganisms.

A film 50B shown in FIG. 1B includes a base film 42B and a synthetic polymer film 34B provided on the base film 42B. The synthetic polymer film 34B has a plurality of raised portions 34Bp over its surface. The plurality of raised portions 34Bp constitute a moth-eye structure. In the film 50B, the configuration of the raised portions 34Bp of the synthetic polymer film 34B is different from that of the raised portions 34Ap of the synthetic polymer film 34A of the film 50A. Descriptions of features which are common with those of the film 50A are sometimes omitted.

When viewed in a normal direction of the synthetic polymer film 34B, the two-dimensional size of the raised portions 34Bp, $D_p$, is in the range of more than 20 nm and less than 500 nm. The typical adjoining distance of the raised portions 34Bp, $D_{int}$, is more than 20 nm and not more than 1000 nm, and $D_p<D_{int}$ holds. That is, in the synthetic polymer film 34B, there is a flat portion between adjoining raised portions 34Bp. The raised portions 34Bp have the shape of a cylinder with a conical portion on the air side. The typical height of the raised portions 34Bp, $D_h$, is not less than 50 nm and less than 500 nm. The raised portions 34Bp may be arranged regularly or may be arranged irregularly. When the raised portions 34Bp are arranged regularly, $D_{int}$ also represents the period of the arrangement. This also applies to the synthetic polymer film 34A, as a matter of course.

In this specification, the "moth-eye structure" includes not only surficial nanostructures that have an excellent antireflection function and that are formed by raised portions which have such a shape that the cross-sectional area (a cross section parallel to the film surface) increases as do the raised portions 34Ap of the synthetic polymer film 34A shown in FIG. 1A but also surficial nanostructures that are formed by raised portions which have a part where the cross-sectional area (a cross section parallel to the film surface) is constant as do the raised portions 34Bp of the synthetic polymer film 34B shown in FIG. 1B. Note that, from the viewpoint of breaking the cell walls and/or cell membranes of microorganisms, providing a conical portion is preferred. Note that, however, the tip end of the conical shape does not necessarily need to be a surficial nanostructure but may have a rounded portion (about 60 nm) which is generally equal to the nanopillars which form surficial nanostructures of the wings of cicadas.

A mold for forming the moth-eye structure such as illustrated in FIG. 1A and FIG. 1B over the surface (hereinafter, referred to as "moth-eye mold") has an inverted moth-eye structure obtained by inverting the moth-eye structure. Using an anodized porous alumina layer which has the inverted moth-eye structure as a mold without any modification enables inexpensive production of the moth-eye structure. Particularly when a moth-eye mold in the shape of a hollow cylinder is used, the moth-eye structure can be efficiently manufactured according to a roll-to-roll method. Such a moth-eye mold can be manufactured according to methods disclosed in Japanese Laid-Open Patent Publication No. 2009-166502, WO 2011/125486 and WO 2013/183576.

A manufacturing method of a moth-eye mold 100A that is for production of the synthetic polymer film 34A is described with reference to FIG. 2A, FIG. 2B, FIG. 2C, FIG. 2D, and FIG. 2E.

Figure 2A:
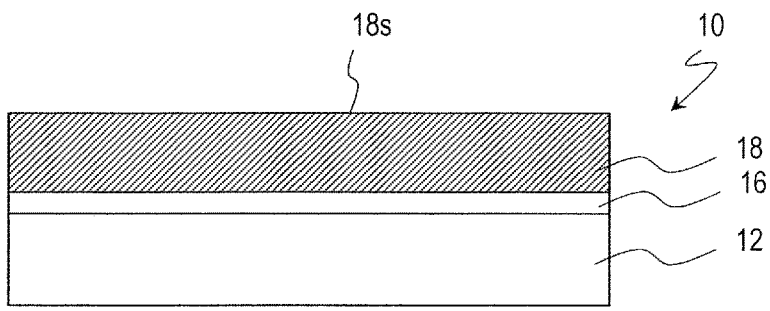
FIG. 2A, FIG. 2B, FIG. 2C, FIG. 2D, and FIG. 2E are diagrams for illustrating a method for manufacturing a moth-eye mold 100A and a configuration of the moth-eye mold 100A.

Firstly, a mold base 10 is provided which includes an aluminum base 12, an inorganic material layer 16 provided on a surface of the aluminum base 12, and an aluminum film 18 deposited on the inorganic material layer 16 as shown in FIG. 2A.

The aluminum base 12 used may be an aluminum base whose aluminum purity is not less than 99.50 mass % and less than 99.99 mass % and which has relatively high rigidity. The impurity contained in the aluminum base 12 may preferably include at least one element selected from the group consisting of iron (Fe), silicon (Si), copper (Cu), manganese (Mn), zinc (Zn), nickel (Ni), titanium (Ti), lead (Pb), tin (Sn) and magnesium (Mg). Particularly, Mg is preferred. Since the mechanism of formation of pits (hollows) in the etching step is a local cell reaction, the aluminum base 12 ideally does not contain any element which is nobler than aluminum. It is preferred that the aluminum base 12 used contains, as the impurity element, Mg (standard electrode potential: −2.36 V) which is a base metal. If the content of an element nobler than aluminum is 10 ppm or less, it can be said in terms of electrochemistry that the aluminum base 12 does not substantially contain the element. The Mg content is preferably 0.1 mass % or more of the whole. It is, more preferably, in the range of not more than about 3.0 mass %. If the Mg content is less than 0.1 mass %, sufficient rigidity cannot be obtained. On the other hand, as the Mg content increases, segregation of Mg is more likely to occur. Even if the segregation occurs near a surface over which a moth-eye mold is to be formed, it would not be detrimental in terms of electrochemistry but would be a cause of a defect because Mg forms an anodized film of a different form from that of aluminum. The content of the impurity element may be appropriately determined depending on the shape, thickness, and size of the aluminum base 12, in view of required rigidity. For example, when the aluminum base 12 in the form of a plate is prepared by rolling, the appropriate Mg content is about 3.0 mass %. When the aluminum base 12 having a three-dimensional structure of, for example, a hollow cylinder is prepared by extrusion, the Mg content is preferably 2.0 mass % or less. If the Mg content exceeds 2.0 mass %, the extrudability deteriorates in general.

The aluminum base 12 used may be an aluminum pipe in the shape of a hollow cylinder which is made of, for example, JIS A1050, an Al—Mg based alloy (e.g., JIS A5052), or an Al—Mg—Si based alloy (e.g., JIS A6063).

The surface of the aluminum base 12 is preferably a surface cut with a bit. If, for example, abrasive particles are remaining on the surface of the aluminum base 12, conduction will readily occur between the aluminum film 18 and the aluminum base 12 in a portion in which the abrasive particles are present. Not only in the portion in which the abrasive particles are remaining but also in a portion which has a roughened surface, conduction is likely to occur locally between the aluminum film 18 and the aluminum base 12. When conduction occurs locally between the aluminum film 18 and the aluminum base 12, there is a probability that a local cell reaction will occur between an impurity in the aluminum base 12 and the aluminum film 18.

The material of the inorganic material layer 16 may be, for example, tantalum oxide ($Ta_2O_5$) or silicon dioxide ($SiO_2$). The inorganic material layer 16 can be formed by, for example, sputtering. When a tantalum oxide layer is used as the inorganic material layer 16, the thickness of the tantalum oxide layer is, for example, 200 nm.

The thickness of the inorganic material layer 16 is preferably not less than 100 nm and less than 500 nm. If the thickness of the inorganic material layer 16 is less than 100 nm, there is a probability that a defect (typically, a void; i.e., a gap between crystal grains) occurs in the aluminum film 18. If the thickness of the inorganic material layer 16 is not less than 500 nm, insulation is likely to occur between the aluminum base 12 and the aluminum film 18 due to the surface condition of the aluminum base 12. To realize anodization of the aluminum film 18 by supplying an electric current from the aluminum base 12 side to the aluminum film 18, the electric current needs to flow between the aluminum base 12 and the aluminum film 18. When employing a configuration where an electric current is supplied from the inside surface of the aluminum base 12 in the shape of a hollow cylinder, it is not necessary to provide an electrode to the aluminum film 18. Therefore, the aluminum film 18 can be anodized across the entire surface, while such a problem does not occur that supply of the electric current becomes more difficult as the anodization advances. Thus, the aluminum film 18 can be anodized uniformly across the entire surface.

To form a thick inorganic material layer 16, it is in general necessary to increase the film formation duration. When the film formation duration is increased, the surface temperature of the aluminum base 12 unnecessarily increases, and as a result, the film quality of the aluminum film 18 deteriorates, and a defect (typically, a void) occurs in some cases. When the thickness of the inorganic material layer 16 is less than 500 nm, occurrence of such a problem can be suppressed.

The aluminum film 18 is, for example, a film which is made of aluminum whose purity is not less than 99.99 mass % (hereinafter, also referred to as "high-purity aluminum film") as disclosed in WO 2011/125486. The aluminum film 18 is formed by, for example, vacuum evaporation or sputtering. The thickness of the aluminum film 18 is preferably in the range of not less than about 500 nm and not more than about 1500 nm. For example, the thickness of the aluminum film 18 is about 1 μm.

The aluminum film 18 may be an aluminum alloy film disclosed in WO 2013/183576 in substitution for the high-purity aluminum film. The aluminum alloy film disclosed in WO 2013/183576 contains aluminum, a metal element other than aluminum, and nitrogen. In this specification, the "aluminum film" includes not only the high-purity aluminum film but also the aluminum alloy film disclosed in WO 2013/183576.

Using the above-described aluminum alloy film can realize a specular surface whose reflectance is not less than 80%. The average grain diameter of crystal grains that form the aluminum alloy film when viewed in the normal direction of the aluminum alloy film is, for example, not more than 100 nm, and that the maximum surface roughness Rmax of the aluminum alloy film is not more than 60 nm. The content of nitrogen in the aluminum alloy film is, for example, not less than 0.5 mass % and not more than 5.7 mass %. It is preferred that the absolute value of the difference between the standard electrode potential of the metal element other than aluminum which is contained in the aluminum alloy film and the standard electrode potential of aluminum is not more than 0.64 V, and that the content of the metal element in the aluminum alloy film is not less than 1.0 mass % and not more than 1.9 mass %. The metal element is, for example, Ti or Nd. The metal element is not limited to these examples but may be such a different metal element that the absolute value of the difference between the standard electrode potential of the metal element and the standard electrode potential of aluminum is not more than 0.64 V (for example, Mn, Mg, Zr, V, and Pb). Further, the metal element may be Mo, Nb, or Hf. The aluminum alloy film may contain two or more of these metal elements. The aluminum alloy film is formed by, for example, a DC magnetron sputtering method. The thickness of the aluminum alloy film is also preferably in the range of not less than about 500 nm and not more than about 1500 nm. For example, the thickness of the aluminum alloy film is about 1 μm.

Figure 2B:
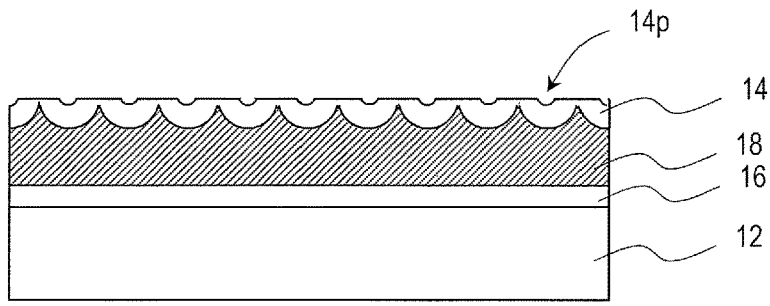

Then, a surface 18s of the aluminum film 18 is anodized to form a porous alumina layer 14 which has a plurality of recessed portions (micropores) 14p as shown in FIG. 2B. The porous alumina layer 14 includes a porous layer which has the recessed portions 14p and a barrier layer (the base of the recessed portions (micropores) 14p). As known in the art, the interval between adjacent recessed portions 14p (the distance between the centers) is approximately twice the thickness of the barrier layer and is approximately proportional to the voltage that is applied during the anodization. This relationship also applies to the final porous alumina layer 14 shown in FIG. 2E.

The porous alumina layer 14 is formed by, for example, anodizing the surface 18s in an acidic electrolytic solution. The electrolytic solution used in the step of forming the porous alumina layer 14 is, for example, an aqueous solution which contains an acid selected from the group consisting of oxalic acid, tartaric acid, phosphoric acid, sulfuric acid, chromic acid, citric acid, and malic acid. For example, the surface 18s of the aluminum film 18 is anodized with an applied voltage of 80 V for 55 seconds using an oxalic acid aqueous solution (concentration: 0.3 mass %, solution temperature: 10° C.), whereby the porous alumina layer 14 is formed.

Figure 2C:
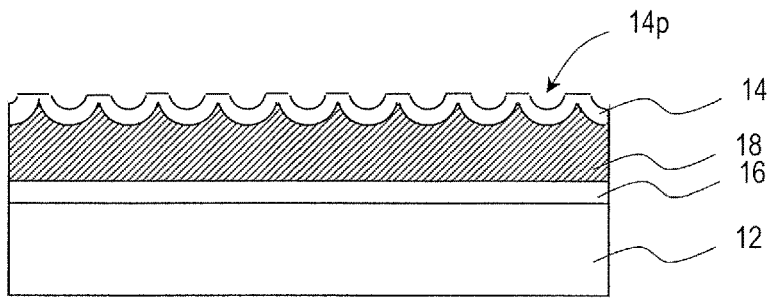

Then, the porous alumina layer 14 is brought into contact with an alumina etchant such that a predetermined amount is etched away, whereby the opening of the recessed portions 14p is enlarged as shown in FIG. 2C. By modifying the type and concentration of the etching solution and the etching duration, the etching amount (i.e., the size and depth of the recessed portions 14p) can be controlled. The etching solution used may be, for example, an aqueous solution of 10 mass % phosphoric acid, organic acid such as formic acid, acetic acid or citric acid, or sulfuric acid, or a chromic/phosphoric acid solution. For example, the etching is performed for 20 minutes using a phosphoric acid aqueous solution (10 mass %, 30° C.)

Figure 2D:
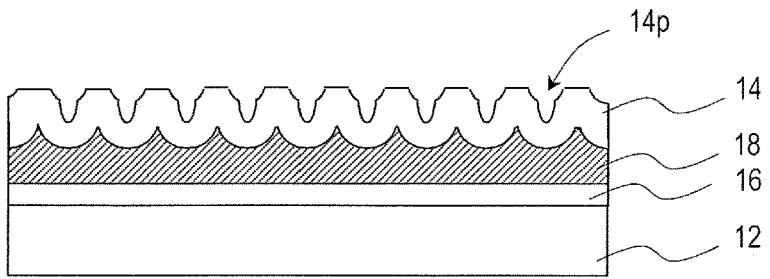

Then, the aluminum film 18 is again partially anodized such that the recessed portions 14p are grown in the depth direction and the thickness of the porous alumina layer 14 is increased as shown in FIG. 2D. Here, the growth of the recessed portions 14p starts at the bottoms of the previously-formed recessed portions 14p, and accordingly, the lateral surfaces of the recessed portions 14p have stepped shapes.

Thereafter, when necessary, the porous alumina layer 14 may be brought into contact with an alumina etchant to be further etched such that the pore diameter of the recessed portions 14p is further increased. The etching solution used in this step may preferably be the above-described etching solution. Practically, the same etching bath may be used.

Figure 2E:
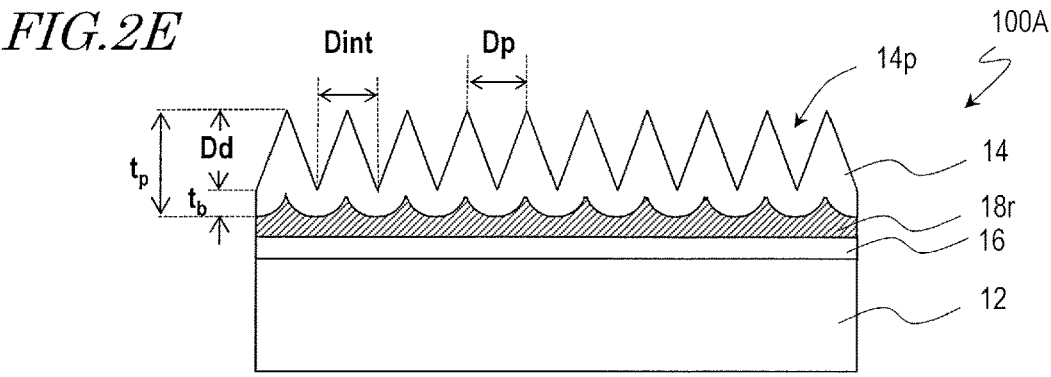

In this way, by alternately repeating the anodization step and the etching step as described above through multiple cycles (e.g., 5 cycles: including 5 anodization cycles and 4 etching cycles), the moth-eye mold 100A that includes the porous alumina layer 14 which has the inverted moth-eye structure is obtained as shown in FIG. 2E. Since the process is ended with the anodization step, the recessed portions 14p have pointed bottom portion. That is, the resultant mold enables formation of raised portions with pointed tip ends.

The porous alumina layer 14 (thickness: $t_p$) shown in FIG. 2E includes a porous layer (whose thickness is equivalent to the depth $D_d$ of the recessed portions 14p) and a barrier layer (thickness: $t_b$). Since the porous alumina layer 14 has a structure obtained by inverting the moth-eye structure of the synthetic polymer film 34A, corresponding parameters which define the dimensions may sometimes be designated by the same symbols.

The recessed portions 14p of the porous alumina layer 14 may have, for example, a conical shape and may have a stepped lateral surface. It is preferred that the two-dimensional size of the recessed portions 14p (the diameter of a circle equivalent to the area of the recessed portions 14p when viewed in a normal direction of the surface), $D_p$, is more than 20 nm and less than 500 nm, and the depth of the recessed portions 14p, $D_d$, is not less than 50 nm and less than 1000 nm (1 μm). It is also preferred that the bottom portion of the recessed portions 14p is acute (with the deepest part of the bottom portion being pointed). When the recessed portions 14p are in a densely packed arrangement, assuming that the shape of the recessed portions 14p when viewed in a normal direction of the porous alumina layer 14 is a circle, adjacent circles overlap each other, and a saddle portion is formed between adjacent ones of the recessed portions 14p. Note that, when the generally-conical recessed portions 14p adjoin one another so as to form saddle portions, the two-dimensional size of the recessed portions 14p, $D_p$, is equal to the adjoining distance $D_{int}$. The thickness of the porous alumina layer 14, $t_p$, is not more than about 1 μm.

Under the porous alumina layer 14 shown in FIG. 2E, there is an aluminum remnant layer 18r. The aluminum remnant layer 18r is part of the aluminum film 18 which has not been anodized. When necessary, the aluminum film 18 may be substantially thoroughly anodized such that the aluminum remnant layer 18r is not present. For example, when the inorganic material layer 16 has a small thickness, it is possible to readily supply an electric current from the aluminum base 12 side.

The manufacturing method of the moth-eye mold illustrated herein enables manufacture of a mold which is for production of antireflection films disclosed in Japanese Laid-Open Patent Publication No. 2009-166502, WO 2011/125486 and WO 2013/183576. Since an antireflection film used in a high-definition display panel is required to have high uniformity, selection of the material of the aluminum base, specular working of the aluminum base, and control of the purity and components of the aluminum film are preferably carried out as described above. However, the above-described mold manufacturing method can be simplified because the microbicidal activity can be achieved without high uniformity. For example, the surface of the aluminum base may be directly anodized. Even if, in this case, pits are formed due to impurities contained in the aluminum base, only local structural irregularities occur in the moth-eye structure of the finally-obtained synthetic polymer film 34A, and it is estimated that there is little adverse influence on the microbicidal activity.

According to the above-described mold manufacturing method, a mold in which the regularity of the arrangement of the recessed portions is low, and which is suitable to production of an antireflection film, can be manufactured. In the case of utilizing the microbicidal ability of the moth-eye structure, it is estimated that the regularity of the arrangement of the raised portions does not exert an influence. A mold for formation of a moth-eye structure which has regularly-arranged raised portions can be manufactured, for example, as described in the following section.

For example, after formation of a porous alumina layer having a thickness of about 10 μm, the formed porous alumina layer is removed by etching, and then, anodization may be performed under the conditions for formation of the above-described porous alumina layer. A 10 μm thick porous alumina layer is realized by extending the anodization duration. When such a relatively thick porous alumina layer is formed and then this porous alumina layer is removed, a porous alumina layer having regularly-arranged recessed portions can be formed without being influenced by irregularities which are attributed to grains that are present at the surface of an aluminum film or aluminum base or the process strain. Note that, in removal of the porous alumina layer, using a chromic/phosphoric acid solution is preferred. Although continuing the etching for a long period of time sometimes causes galvanic corrosion, the chromic/phosphoric acid solution has the effect of suppressing galvanic corrosion.

A moth-eye mold for production of the synthetic polymer film 34B shown in FIG. 1B can be, basically, manufactured by combination of the above-described anodization step and etching step. A manufacturing method of a moth-eye mold 100B that is for production of the synthetic polymer film 34B is described with reference to FIG. 3A, FIG. 3B, and FIG. 3C.

Firstly, in the same way as illustrated with reference to FIG. 2A and FIG. 2B, the mold base 10 is provided, and the surface 18s of the aluminum film 18 is anodized, whereby a porous alumina layer 14 which has a plurality of recessed portions (micropores) 14p is formed.

Figure 3A:
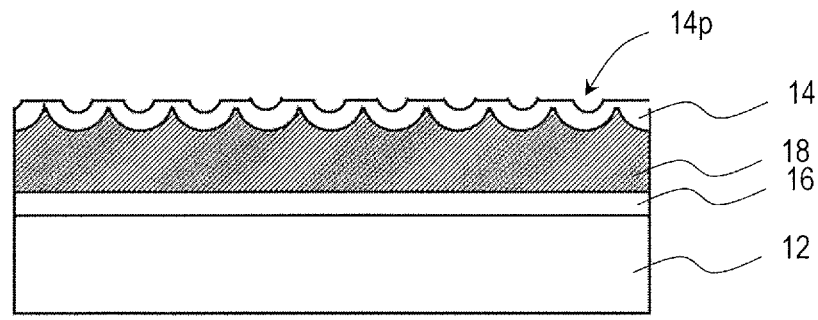
FIG. 3A, FIG. 3B, and FIG. 3C are diagrams for illustrating a method for manufacturing a moth-eye mold 100B and a configuration of the moth-eye mold 100B.

Then, the porous alumina layer 14 is brought into contact with an alumina etchant such that a predetermined amount is etched away, whereby the opening of the recessed portions 14p is enlarged as shown in FIG. 3A. In this step, the etched amount is smaller than in the etching step illustrated with reference to FIG. 2C. That is, the size of the opening of the recessed portions 14p is decreased. For example, the etching is performed for 10 minutes using a phosphoric acid aqueous solution (10 mass %, 30° C.).

Figure 3B:
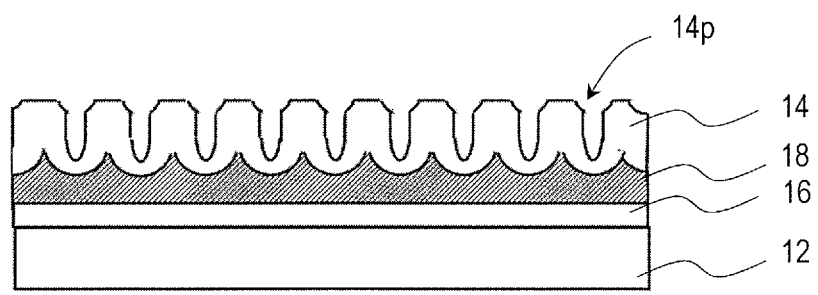

Then, the aluminum film 18 is again partially anodized such that the recessed portions 14p are grown in the depth direction and the thickness of the porous alumina layer 14 is increased as shown in FIG. 3B. In this step, the recessed portions 14p are grown deeper than in the anodization step illustrated with reference to FIG. 2D. For example, the anodization is carried out with an applied voltage of 80 V for 165 seconds (in FIG. 2D, 55 seconds) using an oxalic acid aqueous solution (concentration: 0.3 mass %, solution temperature: 10° C.).

Figure 3C:
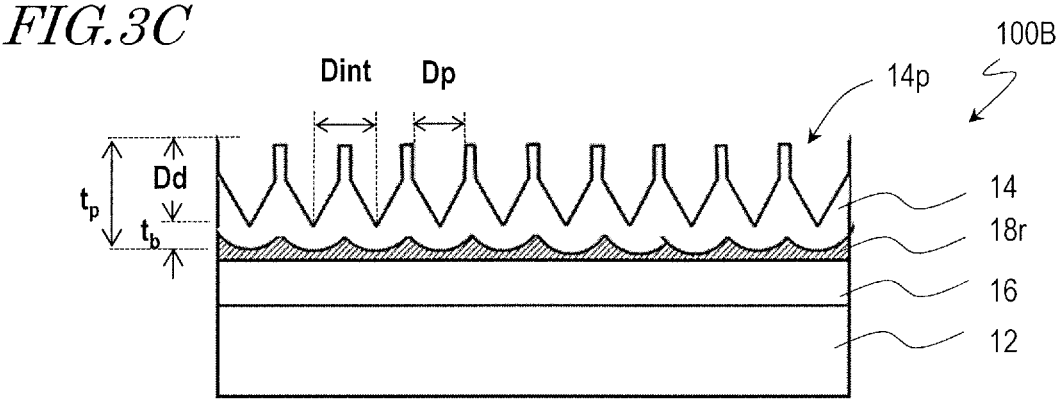

Thereafter, the etching step and the anodization step are alternately repeated through multiple cycles in the same way as illustrated with reference to FIG. 2E. For example, 3 cycles of the etching step and 3 cycles of the anodization step are alternately repeated, whereby the moth-eye mold 100B including the porous alumina layer 14 which has the inverted moth-eye structure is obtained as shown in FIG. 3C. In this step, the two-dimensional size of the recessed portions 14p, $D_p$, is smaller than the adjoining distance $D_{int}$ ($D_p < D_{int}$).

The size of the microorganisms varies depending on their types. For example, the size of *P. aeruginosa* is about 1 µm. However, the size of the bacteria ranges from several hundreds of nanometers to about five micrometers. The size of fungi is not less than several micrometers. For example, it is estimated that raised portions whose two-dimensional size is about 200 nm have a microbicidal activity on a microorganism whose size is not less than about 0.5 µm, but there is a probability that the raised portions are too large to exhibit a sufficient microbicidal activity on a bacterium whose size is several hundreds of nanometers. The size of viruses ranges from several tens of nanometers to several hundreds of nanometers, and many of them have a size of not more than 100 nm. Note that viruses do not have a cell membrane but have a protein shell called capsid which encloses virus nucleic acids. The viruses can be classified into those which have a membrane-like envelope outside the shell and those which do not have such an envelope. In the viruses which have an envelope, the envelope is mainly made of a lipid. Therefore, it is expected that the raised portions likewise act on the envelope. Examples of the viruses which have an envelope include influenza virus and Ebola virus. In the viruses which do not have an envelope, it is expected that the raised portions likewise act on this protein shell called capsid. When the raised portions include nitrogen element, the raised portions can have an increased affinity for a protein which is made of amino acids.

In view of the above, the configuration and production method of a synthetic polymer film having raised portions which can exhibit a microbicidal activity against a microorganism of not more than several hundreds of nanometers are described below.

In the following description, raised portions of the above-described synthetic polymer film which have a two-dimensional size in the range of more than 20 nm and less than 500 nm are referred to as "first raised portions". Raised portions which are superimposedly formed over the first raised portions are referred to as "second raised portions". The two-dimensional size of the second raised portions is smaller than the two-dimensional size of the first raised portions and does not exceed 100 nm. Note that when the two-dimensional size of the first raised portions is less than 100 nm, particularly less than 50 nm, it is not necessary to provide the second raised portions. Recessed portions of the mold corresponding to the first raised portions are referred to as "first recessed portions", and recessed portions of the mold corresponding to the second raised portions are referred to as "second recessed portions".

When the method of forming the first recessed portions which have predetermined size and shape by alternately performing the anodization step and the etching step as described above is applied without any modification, the second recessed portions cannot be formed successfully.

Figure 4A:
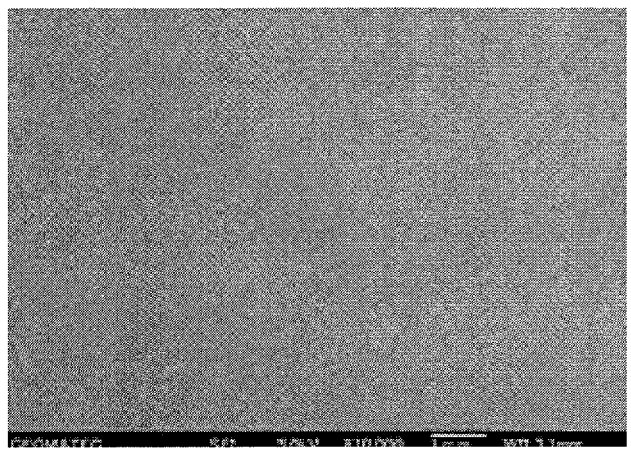
FIG. 4A shows a SEM image of a surface of an aluminum base.
Figure 4B:
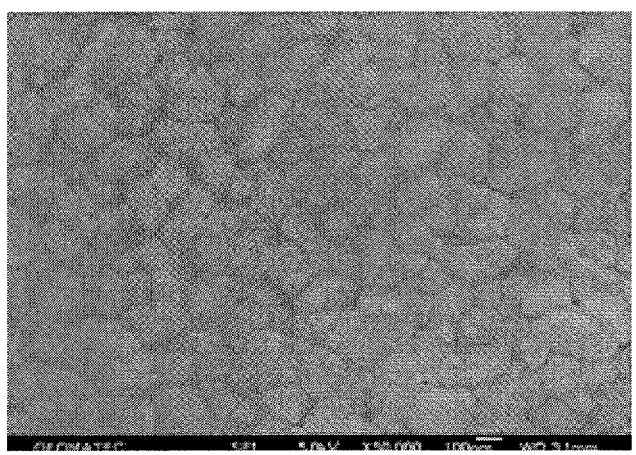
FIG. 4B shows a SEM image of a surface of an aluminum film.
Figure 4C:
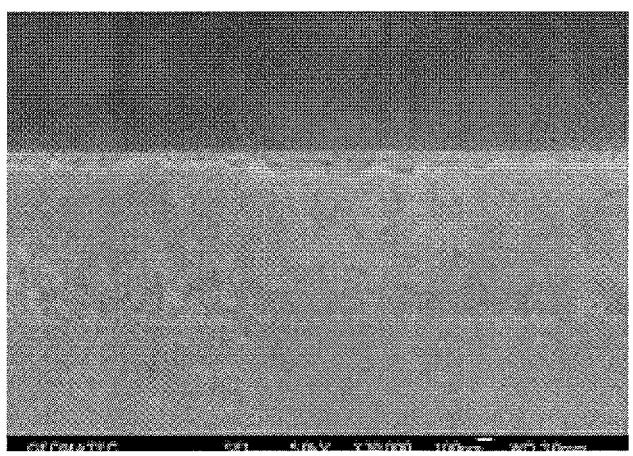
FIG. 4C shows a SEM image of a cross section of the aluminum film.

FIG. 4A shows a SEM image of a surface of an aluminum base (designated by reference numeral 12 in FIG. 2A). FIG. 4B shows a SEM image of a surface of an aluminum film (designated by reference numeral 18 in FIG. 2A). FIG. 4C shows a SEM image of a cross section of the aluminum film (designated by reference numeral 18 in FIG. 2A). As seen from these SEM images, there are grains (crystal grains) at the surface of the aluminum base and the surface of the aluminum film. The grains of the aluminum film form unevenness at the surface of the aluminum film. This unevenness at the surface affects formation of the recessed portions in the anodization and therefore interrupts formation of second recessed portions whose $D_p$ or $D_{int}$ is smaller than 100 nm.

In view of the above, a method for manufacturing a mold which is used in production of a synthetic polymer film according to an embodiment of the present invention includes: (a) providing an aluminum base or an aluminum film deposited on a support; (b) the anodization step of applying a voltage at the first level while a surface of the aluminum base or aluminum film is kept in contact with an electrolytic solution, thereby forming a porous alumina layer which has the first recessed portions; (c) after step (b), the etching step of bringing the porous alumina layer into contact with an etching solution, thereby enlarging the first recessed portions; and (d) after step (c), applying a voltage at the second level that is lower than the first level while the porous alumina layer is kept in contact with an electrolytic solution, thereby forming the second recessed portions in the first recessed portions. For example, the first level is higher than 40 V, and the second level is equal to or lower than 20 V.

Specifically, an anodization step is carried out with the voltage at the first level, whereby the first recessed portions are formed which have such a size that is not influenced by the grains of the aluminum base or aluminum film. Thereafter, the thickness of the barrier layer is decreased by etching, and then, another anodization step is carried out with the voltage at the second level that is lower than the first level, whereby the second recessed portions are formed in the first recessed portions. When the second recessed portions are formed through such a procedure, the influence of the grains is avoided.

Figure 5A:
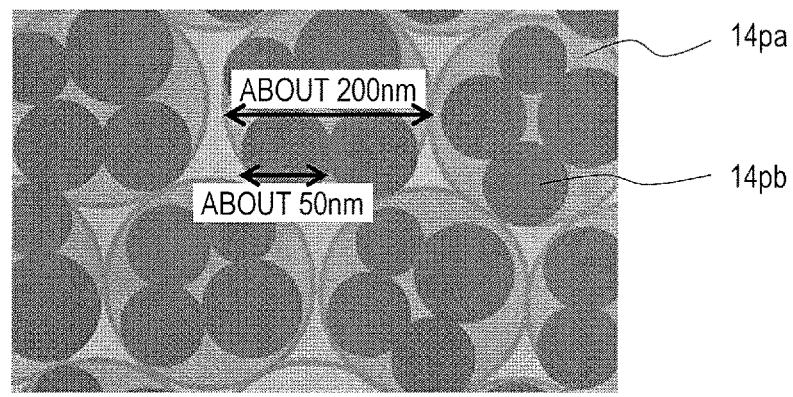
FIG. 5A is a schematic plan view of a porous alumina layer of a mold.
Figure 5B:
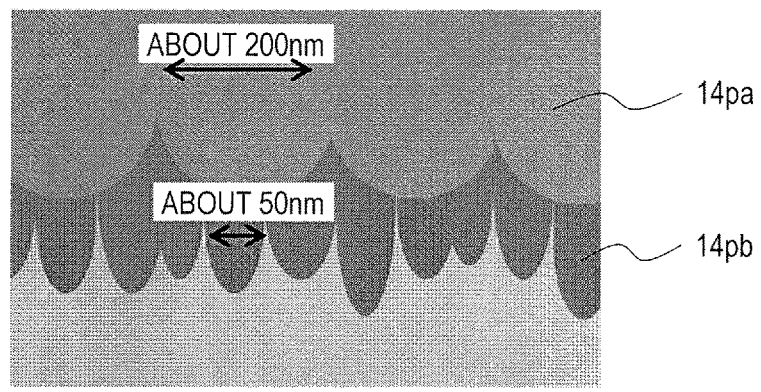
FIG. 5B is a schematic cross-sectional view of the porous alumina layer.
Figure 5C:
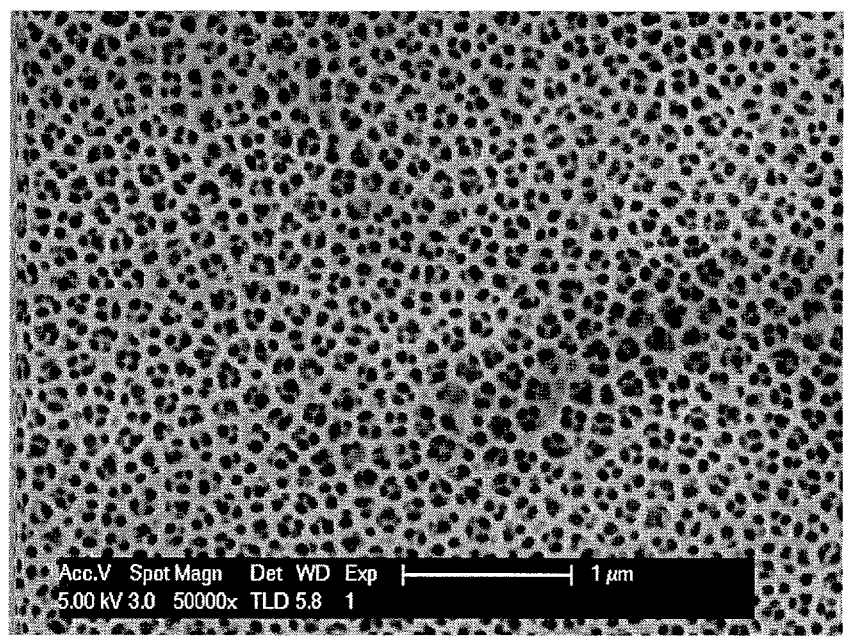
FIG. 5C is a SEM image of a prototype mold.

A mold which has first recessed portions 14*pa* and second recessed portions 14*pb* formed in the first recessed portions 14*pa* is described with reference to FIG. 5A, FIG. 5B, and FIG. 5C. FIG. 5A is a schematic plan view of a porous alumina layer of a mold. FIG. 5B is a schematic cross-sectional view of the porous alumina layer. FIG. 5C shows a SEM image of a prototype mold.

As shown in FIG. 5A and FIG. 5B, the surface of the mold of the present embodiment has the plurality of first recessed portions 14*pa* whose two-dimensional size is in the range of more than 20 nm and less than 500 nm and the plurality of second recessed portions 14*pb* which are superimposedly formed over the plurality of first recessed portions 14*pa*. The two-dimensional size of the plurality of second recessed portions 14*pb* is smaller than the two-dimensional size of the plurality of first recessed portions 14*pa* and does not exceed 100 nm. The height of the second recessed portions 14*pb* is, for example, more than 20 nm and not more than 100 nm. The second recessed portions 14*pb* preferably have a generally conical portion as do the first recessed portions 14*pa*.

The porous alumina layer shown in FIG. 5C was formed as described below.

The aluminum film used was an aluminum film which contains Ti at 1 mass %. The anodization solution used was an oxalic acid aqueous solution (concentration: 0.3 mass %, solution temperature: 10° C.). The etching solution used was a phosphoric acid aqueous solution (concentration: 10 mass %, solution temperature: 30° C.). After the anodization was carried out with a voltage of 80 V for 52 seconds, the etching was carried out for 25 minutes. Then, the anodization was carried out with a voltage of 80 V for 52 seconds, and the etching was carried out for 25 minutes. Thereafter, the anodization was carried out with a voltage of 20 V for 52 seconds, and the etching was carried out for 5 minutes. Further, the anodization was carried out with a voltage of 20 V for 52 seconds.

As seen from FIG. 5C, the second recessed portions whose $D_p$ was about 50 nm were formed in the first recessed portions whose $D_p$ was about 200 nm. When in the above-described manufacturing method the voltage at the first level was changed from 80 V to 45 V for formation of the porous alumina layer, the second recessed portions whose $D_p$ was about 50 nm were formed in the first recessed portions whose $D_p$ was about 100 nm.

When a synthetic polymer film is produced using such a mold, the produced synthetic polymer film has raised portions whose configuration is the inverse of that of the first recessed portions 14pa and the second recessed portions 14pb shown in FIG. 5A and FIG. 5B. That is, the produced synthetic polymer film further includes a plurality of second raised portions superimposedly formed over a plurality of first raised portions.

The thus-produced synthetic polymer film which has the first raised portions and the second raised portions superimposedly formed over the first raised portions has a microbicidal activity on various microorganisms, ranging from relatively small microorganisms of about 100 nm to relatively large microorganisms of not less than 5 μm.

As a matter of course, only raised portions whose two-dimensional size is in the range of more than 20 nm and less than 100 nm may be formed according to the size of a target microorganism. The mold for formation of such raised portions can be manufactured, for example, as described below.

The anodization is carried out using a neutral salt aqueous solution (ammonium borate, ammonium citrate, etc.), such as an ammonium tartrate aqueous solution, or an organic acid which has a low ionic dissociation degree (maleic acid, malonic acid, phthalic acid, citric acid, tartaric acid, etc.) to form a barrier type anodized film. After the barrier type anodized film is removed by etching, the anodization is carried out with a predetermined voltage (the voltage at the second level described above), whereby recessed portions whose two-dimensional size is in the range of more than 20 nm and less than 100 nm can be formed.

For example, an aluminum film which contains Ti at 1 mass % is anodized at 100 V for 2 minutes using a tartaric acid aqueous solution (concentration: 0.1 mol/L, solution temperature: 23° C.), whereby a barrier type anodized film is formed. Thereafter, the etching is carried out for 25 minutes using a phosphoric acid aqueous solution (concentration: 10 mass %, solution temperature: 30° C.), whereby the barrier type anodized film is removed. Thereafter, the anodization and the etching are alternatively repeated as described above, specifically through 5 anodization cycles and 4 etching cycles. The anodization was carried out at 20 V for 52 seconds using an oxalic acid aqueous solution (concentration: 0.3 mass %, solution temperature: 10° C.) as the anodization solution. The etching was carried out for 5 minutes using the above-described etching solution. As a result, recessed portions whose two-dimensional size is about 50 nm can be uniformly formed.

Moth-eye molds which are capable of forming various moth-eye structures can be manufactured as described above.

Figure 6:
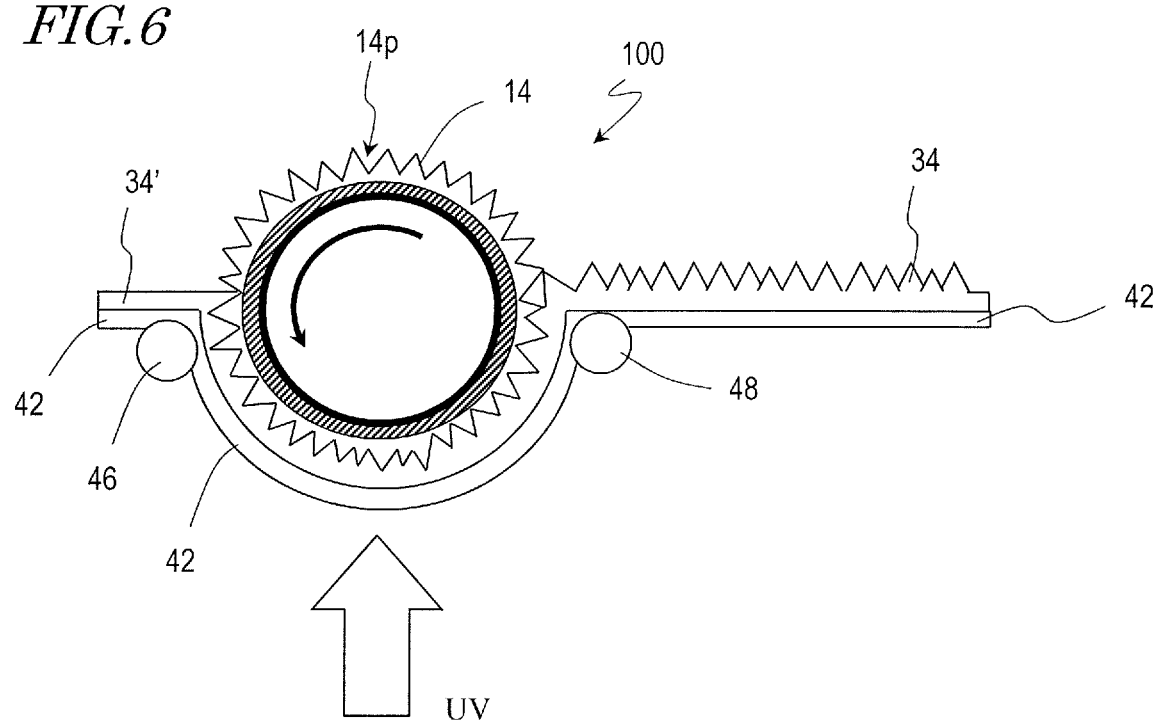
FIG. 6 is a diagram for illustrating a method for producing a synthetic polymer film with the use of the moth-eye mold 100.

Next, a method for producing a synthetic polymer film with the use of a moth-eye mold 100 is described with reference to FIG. 6. FIG. 6 is a schematic cross-sectional view for illustrating a method for producing a synthetic polymer film according to a roll-to-roll method. In the following paragraphs, a method for producing a synthetic polymer film over a surface of a base film as a work using the above-described roll mold will be described. However, a synthetic polymer film production method according to an embodiment of the present invention is not limited to this example but is capable of producing a synthetic polymer film over a surface of various types of works using a mold of a different shape.

First, a moth-eye mold 100 in the shape of a hollow cylinder is provided. Note that the moth-eye mold 100 in the shape of a hollow cylinder is manufactured according to, for example, the manufacturing method described with reference to FIG. 2A, FIG. 2B, FIG. 2C, FIG. 2D, and FIG. 2E.

As shown in FIG. 6, a base film 42 over which a UV-curable resin 34' is applied on its surface is maintained pressed against the moth-eye mold 100, and the UV-curable resin 34' is irradiated with ultraviolet (UV) light such that the UV-curable resin 34' is cured. The UV-curable resin 34' used may be, for example, an acrylic resin. The base film 42 may be, for example, a PET (polyethylene terephthalate) film or a TAC (triacetyl cellulose) film. The base film 42 is fed from an unshown feeder roller, and thereafter, the UV-curable resin 34' is applied over the surface of the base film 42 using, for example, a slit coater or the like. The base film 42 is supported by supporting rollers 46 and 48 as shown in FIG. 6. The supporting rollers 46 and 48 have rotation mechanisms for carrying the base film 42. The moth-eye mold 100 in the shape of a hollow cylinder is rotated at a rotation speed corresponding to the carrying speed of the base film 42 in a direction indicated by the arrow in FIG. 6.

Thereafter, the moth-eye mold 100 is separated from the base film 42, whereby a synthetic polymer film 34 to which the inverted moth-eye structure of the moth-eye mold 100 is transferred is formed on the surface of the base film 42. The base film 42 which has the synthetic polymer film 34 formed on the surface is wound up by an unshown winding roller.

The surface of the synthetic polymer film 34 has the moth-eye structure obtained by inverting the surficial nanostructures of the moth-eye mold 100. According to the surficial nanostructure of the moth-eye mold 100 used, the synthetic polymer films 34A and 34B shown in FIG. 1A and FIG. 1B, respectively, can be produced. The material that forms the synthetic polymer film 34 is not limited to the UV-curable resin but may be a photocurable resin which is curable by visible light.

The microbicidal ability of a synthetic polymer film which has the moth-eye structure over its surface has not only a correlation with the physical structure of the synthetic polymer film but also a correlation with the chemical properties of the synthetic polymer film. For example, the present applicant found correlations with chemical properties, such as a correlation with the contact angle of the surface of the synthetic polymer film (WO 2015/163018), a correlation with the concentration of the nitrogen element contained in the surface (WO 2016/080245), and a correlation with the content of ethylene oxide units ($-CH_2CH_2O-$) in addition to the nitrogen element concentration (WO 2016/208540).

Figure 7A:
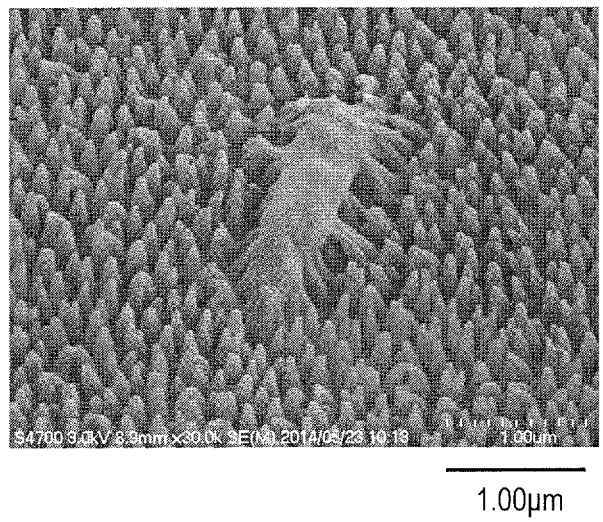
FIG. 7A and FIG. 7B show SEM images obtained by SEM (Scanning Electron Microscope) observation of a *P. aeruginosa* bacterium which died at a surface which had a moth-eye structure.
Figure 7B:
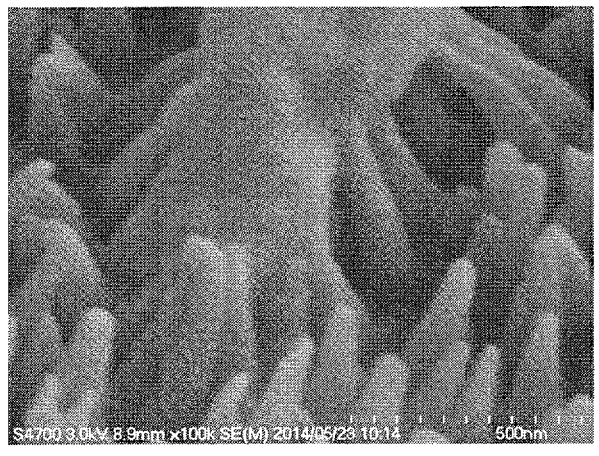

FIG. 7A and FIG. 7B shows SEM images disclosed in WO 2016/080245 (FIG. 8). FIG. 7A and FIG. 7B show SEM images obtained by SEM (Scanning Electron Microscope) observation of a *P. aeruginosa* bacterium which died at the surface which had the moth-eye structure shown in FIG. 1A.

As seen from these SEM images, the tip end portions of the raised portions enter the cell wall (exine) of a *P. aeruginosa* bacterium. In FIG. 7A and FIG. 7B, the raised portions do not appear to break through the cell wall but appears to be taken into the cell wall. This might be explained by the mechanism suggested in the "Supplemental Information" section of Ivanova, E. P. et al. That is, it is estimated that the exine (lipid bilayer) of the Gram-negative bacteria came close to the raised portions and deformed so that the lipid bilayer locally underwent a transition like a first-order phase transition (spontaneous reorientation) and openings were formed in portions close to the raised portions, and the raised portions entered these openings. Alternatively, it is estimated that the raised portions were taken in due to the cell's mechanism of taking a polar substance (including a nutrient source) into the cell (endocytosis).

The present inventors further studied a synthetic polymer film which is suitably used for sterilization of a liquid including water and found that the synthetic polymer films disclosed in WO 2015/163018, WO 2016/080245 and WO 2016/208540 still have room for improvement in mass productivity (transferability). One of the possible reasons is that the synthetic polymer films disclosed in WO 2015/163018, WO 2016/080245 and WO 2016/208540 are formed using a photocurable resin which contains an acrylate which has a urethane bond. The acrylate which has a urethane bond has relatively high viscosity and is therefore likely to deteriorate the mold releasability. Thus, for example, such an acrylate causes deterioration of the productivity in mass production based on a roll-to-roll method.

From the viewpoint of mass productivity and water resistance, a synthetic polymer film which includes none of a nitrogen element and a fluorine element is preferred as disclosed in International Application No. PCT/JP2018/030788 of the present applicant. A compound including a quaternary ammonium salt, an amino group, or an amide group, which contains a nitrogen element, has high permeability to the mold releasing agent. Therefore, there is a concern that the compound may deteriorate the mold releasability. Thus, for example, it causes deterioration of the productivity in mass production based on a roll-to-roll method. Also, the compound which contains a nitrogen element has high polarity and therefore disadvantageously affects the water resistance. Note that, of the amino groups (amines), the tertiary amino group (tertiary amine) has lower polarity than the primary and secondary amino groups (amines) and therefore exerts a smaller adverse influence on the mass productivity (transferability) and/or water resistance. On the other hand, when an acrylate which contains a fluorine element is used, the acrylate advantageously affects the mold releasability but the synthetic polymer film has high water repellency so that water is unlikely to permeate the acrylate. As a result, there is a concern that the effect of sterilizing a liquid including water may decrease. The entire disclosure of International Application No. PCT/JP2018/030788 is incorporated by reference in this specification.

Since the nitrogen element has a characteristic which improves the microbicidal activity, there is a concern that a synthetic polymer film which does not contain the nitrogen element may have a decreased microbicidal activity. However, as disclosed in International Application No. PCT/JP2018/030788, a synthetic polymer film whose surface has a microbicidal activity and of which the crosslink structure contains none of a nitrogen element and a fluorine element can be obtained.

The present inventors formed synthetic polymer films using photocurable resins of different compositions and evaluated the synthetic polymer films as to the microbicidal ability. The present inventors found that, when a synthetic polymer film contains a certain type of organic carboxylic acid, the microbicidal ability achieved by the surface which has the moth-eye structure improves. The organic carboxylic acid only needs to be contained in the synthetic polymer film. The photocurable resin may generate an organic carboxylic acid by photodecomposition. A compound which generates an organic carboxylic acid by photodecomposition may be an initiator (photopolymerization initiator) or may be a compound which does not function as an initiator (herein referred to as "photoacid generator"). When a radically-polymerizable photocurable resin is used as the photocurable resin, a photoacid generator which generates an organic carboxylic acid without generating a radical may be used.

The organic carboxylic acid and/or the compound which generates an organic carboxylic acid by photodecomposition (initiator and/or photoacid generator) may be mixed in the photocurable resin composition such that the proportion of the organic carboxylic acid and/or the compound to the entirety of the photocurable resin composition is generally equal to or greater than 1 mass % and not more than 10 mass %. If the proportion is less than 1 mass %, the effect of improving the microbicidal ability cannot be achieved sometimes. If the proportion is more than about 10 mass %, there is a concern that the organic carboxylic acid may deteriorate the physical properties of the cured material (photocured resin composition). To suppress the influence on the physical properties of the cured material, it is preferred that the proportion is not more than about 5 mass %. Specifically, according to the type of the photocurable resin and the type of the organic carboxylic acid and/or the compound which generates an organic carboxylic acid by photodecomposition, the amount of the contained organic carboxylic acid and/or compound may be properly adjusted.

An organic carboxylic acid of a certain type has a microbicidal ability (or antimicrobial ability) and is used as, for example, food preservatives. It is supposed that the organic carboxylic acid exhibits the microbicidal ability (antimicrobial ability) through various mechanisms. The mechanisms include (1) decreasing the pH in the environment; and (2) allowing undissociated acid to pass through a cell membrane such that the pH inside the cell decreases. In mechanism (2), a weaker acid (an acid having a smaller dissociation constant) contributes more greatly. See, for example, Rosa M. Raybaudi-Massilia et al., "Control of Pathogenic and Spoilage Microorganisms in Fresh-cut Fruits and Fruit Juices by Traditional and Alternative Natural Antimicrobials", COMPREHENSIVE REVIEWS IN FOOD SCIENCE AND FOOD SAFETY, Vol. 8, pp. 157-180, 2009 (particularly, p. 162).

As will be described later with experimental examples, it is supposed that the microbicidal ability of a synthetic polymer film of an embodiment of the present invention which contains an organic carboxylic acid is improved by the above-described mechanisms (1) and (2).

A synthetic polymer film of an embodiment of the present invention can be mass-produced according to a roll-to-roll method. Therefore, in consideration of the mass productivity, it is preferred to use a synthetic polymer film of which the crosslink structure does not contain any nitrogen element (that is a constituent of a urethane bond) as described above. However, the synthetic polymer film of an embodiment of the present invention is not limited to this example but can be produced by various methods, and therefore, the crosslink structure may contain a nitrogen element.

[Synthetic Polymer Film]

Sample films which had the same configuration as the film 50A shown in FIG. 1A were produced using UV-curable resins of different compositions. The used materials are shown in TABLE 1.

Sample films of the synthetic polymer films of Reference Example which contained a nitrogen element as the synthetic polymer films disclosed in WO 2015/163018, WO 2016/080245 and WO 2016/208540, Examples 1 to 16 of an embodiment of the present invention, and Comparative Examples 1 to 6 were produced. The composition of Reference Example is shown in TABLE 2. The compositions of Examples 1 to 16 are shown in TABLE 3. The compositions of Comparative Examples 1 to 6 are shown in TABLE 4. In Example 15, the resin composition used was prepared by adding water to the same UV-curable resin composition as that used in Example 3. Since it is expected that water hardly remains in the synthetic polymer film, it is not included in the composition shown in TABLE 3. The amount of the added water was 5 g with respect to 100 g acrylic monomer (M280). Assuming that all the constituents of the composition including water constitute 100%, the composition was M280: 93.9%, 819: 1.4%, water: 4.7%.

As the base film 42A, a 50 μm thick PET film (A4300 manufactured by TOYOBO CO., LTD.) was used. The same synthetic polymer film production method as that previously described with reference to FIG. 6 was used to produce a synthetic polymer film 34A which had the moth-eye structure over the surface with the use of the moth-eye mold 100A. The exposure amount was about 200 mJ/cm$^2$ (on the basis of light at the wavelength of 375 nm). In each sample film, $D_p$ was about 200 nm, $D_{int}$ was about 200 nm, and $D_h$ was about 150 nm. In each sample, the synthetic polymer film was produced without using a solvent.

TABLE 1

| MATERIALS | Abbreviation | Product Name | Manufacturer Name | Compound Name | Water Solubility | EO group | MW | Number of moles of EO | EO mass % |
|---|---|---|---|---|---|---|---|---|---|
| Monomer | M280 | M280 | MIWON | polyethylene glycol (400) diacrylate | YES | YES | 508 | 9 | 78 |
|  | M282 | M282 | MIWON | polyethylene glycol (200) diacrylate | YES | YES | 308 | 4 | 57 |
|  | ACMO | ACMO | KJ Chemicals Corporation | acryloylmorpholine | YES | NO | 141 | — | — |
|  | APG400 | APG400 | Shin Nakamura Chemical Co., Ltd. | polypropylene glycol (400) diacrylate | NO | NO | 390 | — | — |
| Polymerization Initiator | TPO | IRGACURE TPO | IGM Resins | diphenyl(2,4,6-trimethylbenzoyl) phosphine oxide | — | — | — | — | — |
|  | 819 | IRGACURE 819 | IGM Resins | bis(2,4,6-trimethylbenzoyl)-phenylphosphine oxide | — | — | — | — | — |
|  | OXE01 | IRGACURE OXE01 | BASF | 1,2-Octanedione, 1-[4-(phenylthio) phenyl]-, 2-(o-benzoyloxime) | — | — | — | — | — |
|  | OXE02 | IRGACURE OXE02 | BASF | ethanone,1-[9-ethyl-6-(2-methylbenzoyl)-9H-carbazol-3-yl],-1-(O-acetyloxime) | — | — | — | — | — |
| Organic Acid | TMBA | Product code: T1421 | Tokyo Chemical Industry Co., Ltd. | 2,4,6-trimethylbenzoic acid | 6 | — | — | — | — |
|  | Succinic Acid | Product code: S0100 | Tokyo Chemical Industry Co., Ltd. | butanedioic acid | 3 | — | — | — | — |
|  | Adipic Acid | Product code: A0161 | Tokyo Chemical Industry Co., Ltd. | hexanedioic acid | 4 | — | — | — | — |
|  | Suberic Acid | Product code: O0023 | Tokyo Chemical Industry Co., Ltd. | octanedioic acid | 5 | — | — | — | — |
|  | Sebacic Acid | Product code: S0022 | Tokyo Chemical Industry Co., Ltd. | decanedioic acid | 6 | — | — | — | — |
|  | Dodecanedioic Acid | Product code: D0013 | Tokyo Chemical Industry Co., Ltd. | dodecanedioic acid | 7 | — | — | — | — |
|  | Acetic Acid | Product code: A2035 | Tokyo Chemical Industry Co., Ltd. | acetic acid | 1 | — | — | — | — |
|  | PPA | Product code: B0026 | Tokyo Chemical Industry Co., Ltd. | phenylphosphate | 1 | — | — | — | — |
| Mold Releasing Agent | SAG003 | Silface SAG003 | Nissin Chemical Industry Co., Ltd. | silicone-based surfactant | — | unknown | — | — | — |
|  | MT70 | FOMBLIN MT70 | SOLVAY | perfluoropolyether derivative; 80% methyl ethyl ketone (solvent); 20% | — | unknown | — | — | — |

In TABLE 1, the numbers in the column of "Water Solubility" for the organic acids represent the solubility index defined below.

The solubility of a solute in water at about 20° C. to about 25° C. are represented based on the amount of water required for dissolving 1 g or 1 mL of the solute using the solubility index (1 to 7) and the terms shown below.

1: Very soluble
Less than 1 mL
2: Freely soluble
Equal to or greater than 1 mL and less than 10 mL
3: Soluble
Equal to or greater than 10 mL and less than 30 mL
4: Sparingly soluble
Equal to or greater than 30 mL and less than 100 mL
5: Slightly soluble
Equal to or greater than 100 mL and less than 1000 mL
6: Very slightly soluble
Equal to or greater than 1000 mL and less than 10000 mL
7: Practically insoluble
Not less than 10000 mL

TABLE 2

| REFERENCE | Acrylic Monomer | | Initiator | |
|---|---|---|---|---|
| EXAMPLES | UA7100 | ATM3LM | ACMO | 819 | TPO |
| Reference Example | 50.3% | 17.7% | 29.1% | 1.5% | 1.5% |

TABLE 3

| EXAMPLES | Acrylic Monomer | | Initiator | | | | Mold Releasing Agent | Additive | | | | |
| | M280 | ACMO | 819 | TPO | OXE01 | OXE02 | SAG003 | TMBA | Succinic acid | Adipic acid | Suberic acid | Sebacic acid | PPA |
|---|---|---|---|---|---|---|---|---|---|---|---|---|---|
| Example 1 | 97.1% | | 2.9% | | | | | | | | | | |
| Example 2 | 98.0% | | 2.0% | | | | | | | | | | |
| Example 3 | 98.5% | | 1.5% | | | | | | | | | | |
| Example 4 | 99.0% | | 1.0% | | | | | | | | | | |
| Example 5 | 97.1% | | | 2.9% | | | | | | | | | |
| Example 6 | 98.0% | | | 2.0% | | | | | | | | | |
| Example 7 | 97.1% | | | | 2.9% | | | | | | | | |
| Example 8 | 98.0% | | | | 2.0% | | | | | | | | |
| Example 9 | 97.6% | | | | | 2.0% | | 0.5% | | | | | |
| Example 10 | 94.6% | 2.9% | | | | 2.0% | | | 0.5% | | | | |
| Example 11 | 94.6% | 2.9% | | | | 2.0% | | | | 0.5% | | | |
| Example 12 | 94.6% | 2.9% | | | | 2.0% | | | | | 0.5% | | |
| Example 13 | 94.6% | 2.9% | | | | 2.0% | | | | | | 0.5% | |
| Example 14 | 97.1% | | | | | 1.9% | | 0.5% | | | | | 0.5% |
| Example 15 | 98.5% | | 1.5% | | | | | | | | | | |
| Example 16 | 97.6% | | 1.5% | | | | 1.0% | | | | | | |

TABLE 4

| COMPARATIVE EXAMPLES | Acrylic Monomer | | | Initiator | | Mold Releasing Agent MT70 (effective constituent) | Additive | | |
| | M280 | ACMO | APG400 | 819 | OXE02 | | Dodecanedioic acid | Acetic acid | PPA |
|---|---|---|---|---|---|---|---|---|---|
| Comparative Example 1 | 98.0% | | | | 2.0% | | | | |
| Comparative Example 2 | 94.6% | 2.9% | | | 2.0% | | 0.5% | | |
| Comparative Example 3 | 97.6% | | | | 2.0% | | | 0.5% | |

TABLE 4-continued

| COMPARATIVE EXAMPLES | Acrylic Monomer | | | Initiator | | Mold Releasing Agent MT70 (effective constituent) | Additive | | |
|---|---|---|---|---|---|---|---|---|---|
| | M280 | ACMO | APG400 | 819 | OXE02 | | Dodecanedioic acid | Acetic acid | PPA |
| Comparative Example 4 | 97.6% | | | 2.0% | | | | | 0.5% |
| Comparative Example 5 | 97.6% | | | 1.5% | | 1.0% | | | |
| Comparative Example 6 | | | 98.5% | 1.5% | | | | | |

Evaluation results of the respective sample films as to the microbicidal ability, the transferability and the film surface properties are shown in TABLE 5 to TABLE 7. TABLE 5 shows the results of Reference Example. TABLE 6 shows the results of Examples 1 to 16. TABLE 7 shows the results of Comparative Examples 1 to 6. The evaluated film surface properties were the spreadability of a water drop over the surface of the synthetic polymer film and the change of the pH of the water drop.

[Evaluation of Microbicidal Ability]

The sample films were evaluated as to the microbicidal ability for the bacterial solution (water) sprinkled over the sample films. The sample films to which the bacterial solution was applied and which were left in atmospheric air at room temperature were evaluated as to the microbicidal ability. Herein, the microbicidal ability for *Staphylococcus aureus* was evaluated. A specific evaluation method is described in the following paragraphs. For each sample film, an experiment was carried out with N=3.

Beforehand, each sample film was left for two weeks in an environment of 25° C. and RH 50% or in an environment of 60° C. and RH 90%. Thereafter, the surface of the sample film was wiped with a BEMCOT wiper (cupro continuous-filament nonwoven fabric manufactured by Asahi Kasei Corporation) impregnated with ethanol.

(1) A bacterial solution including *Staphylococcus aureus* was prepared using 1/500 NB culture medium such that the initial bacteria count was 1E+06 CFU/mL.

(2) On each sample film (a square of 5 cm on each side), 10 μL of the above-described bacterial solution was dropped.

(3) The sample films were left in atmospheric air at room temperature (about 25° C.) for 15 minutes and, thereafter, a SCDLP culture medium was flowed over the sample films to wash away the bacteria (post-wash solution).

(4) The post-wash solution was appropriately diluted with PBS and cultured in the standard agar medium, and the number of bacteria was counted.

The microbicidal ability was evaluated relative to the microbicidal ability of a reference film. The reference film used was a 50 μm thick PET film (A4300 manufactured by TOYOBO CO., LTD.) which was used as the base film. For the PET film, the number of bacteria was counted through the above-described procedure. Each of the sample films was evaluated as to the microbicidal ability in the proportion (%) of the number of bacteria on each sample film to the number of bacteria on the PET film. Specifically, the bacteria survival rate was calculated by the following formula:

Bacteria Survival Rate (%)=Number of bacteria on each sample film (aggregate of N=3)/Number of bacteria on PET film (aggregate of N=3)×100

The criteria for judgement as to the microbicidal ability were based on the bacteria survival rate for each of the condition of 25° C. and RH 50% and the condition of 60° C. and RH 90% such that •: 0%, ○: more than 0% and less than 10%, Δ: not less than 10% and less than 50%, x: not less than 50%. Specifically, when the bacteria survival rate was less than 50%, the sample film was judged to be usable.

[Evaluation of Transferability]

For evaluation of the transferability, an aluminum film (thickness: about 1 μm) was formed on a glass substrate (about 5 cm×about 5 cm), and anodization and etching were performed alternately and repeatedly on the aluminum film, whereby a porous alumina layer ($D_p$ was about 200 nm, $D_{int}$ was about 200 nm, and $D_h$ was about 150 nm) which is the same as that previously described was formed. The surface of the resultant porous alumina layer was subjected to oxygen plasma cleaning (100 W, 25 seconds) such that the contact angle with respect to water was adjusted to 125° to 130°. This is for the purpose of reducing the mold releasability of the mold surface with respect to the UV-curable resin.

A synthetic polymer film was formed ten times on a PET film using a UV-curable resin. Forming a synthetic polymer film on a PET film is represented as "transferring a synthetic polymer film on a PET film". In the ultraviolet light irradiation, a UV lamp manufactured by Fusion UV Systems (product name: LIGHT HANMAR6J6P3) was used. The exposure amount was about 200 mJ/cm² (on the basis of light at the wavelength of 375 nm). The transfer was manually carried out ten times. The lightness in transfer (the magnitude of the force required to pull off the mold from the synthetic polymer film) and the state of the surface of the mold in transfer were considered as indices.

•: The mold was lightly removed from the first transfer to the tenth transfer.

○: The mold was lightly removed in the early transfers, but subsequently the removal gradually became heavier.

Δ: Removal of the mold was already heavy in the early transfers but a failure, such as remaining of the synthetic polymer film (UV-curable resin) on the mold surface, did not occur.

x: In the ten transfers, a failure occurred, such as remaining of the synthetic polymer film on the mold surface.

When •, ○ or Δ, the synthetic polymer film was judged to be usable.

[Evaluation of Film Surface Properties: Degree of Spread of Water Over Synthetic Polymer Film and pH Measurement]

Deionized water was adjusted to pH=7.0±0.1 using 0.01 mol/L hydrochloric acid solution and 0.011 mol/L sodium hydroxide solution. That is, neutral water was prepared in this way.

On the surface of each sample film, a 0.2 cc (200 μL) drop of the above-described pH-adjusted water was placed using a micropipette. Thereafter, the maximum spread diameter (area equivalent circle diameter) up to 5 min was measured, and the average value for five measurements from each sample film was evaluated.

The measurement of the pH was carried out as follows.

In the same way as that described above, on the surface of each sample film, a 0.2 cc (200 μL) drop of the above-described pH-adjusted water was placed using a micropipette. After the passage of 5 minutes, the aqueous solution (water in which an extract from the synthetic polymer film was dissolved) on the surface of each sample film was measured using an electrode for flat samples which is described below, and the average value for five measurements from each sample film was evaluated.

Note that a sample film over which the spread of the water was less than 20 mm was evaluated using a sampling sheet otherwise the diameter of the water drop increased in the pH measurement.

Electrode: pH electrode, product number: 0040-10D (semiconductor sensor) manufactured by HORIBA, Ltd.

Sampling sheet: sampling sheet B, product number: Y011A manufactured by HORIBA, Ltd.

[Identification of Acid]

An acid extracted from each sample film to water was identified as described below using GC-MS (gas chromatograph mass spectrometer).

10 mL THF per 100 $cm^2$ of each sample film was put into a glass container. The sample film was immersed in THF at 50° C. for 3 days. Then, THF was passed through a 0.45 μm membrane filter.

0.1 mL of the filtered solution was condensed in a pyrolysis sample cup. The condensed solution was methylated by adding a 10 μL methylating agent (Tetramethylammonium Hydroxide) aqueous solution. Thereafter, the measurement was carried out under the following conditions.

Pyrolyzer: EGA/PY-3030D manufactured by FRONTIER LAB

Conditions: 400° C./30 sec

GC-MS apparatus: 7890A(GC) 5975C(MS) manufactured by Agilent Technologies

Column: UA5HT-30M-0.1F manufactured by FRONTIER LAB

Conditions: Oven 40° C.->320° C. (20° C./min)

Column flow rate: 1 mL/min

Split ratio: 100:1

TABLE 5

| REFERENCE EXAMPLES | Film | Transferability | Acid Type | Film Surface Properties | | Microbicidal Ability | | | |
|---|---|---|---|---|---|---|---|---|---|
| | | | | Water Spread (mm) | pH | Normal Temperature | | High Temperature, High Humidity | |
| | | | | | | Bacteria Survival Rate (%) | Judge | Bacteria Survival Rate (%) | Judge |
| Reference Example | moth-eye | x | TMBA/DPPA | 28.5 | 3.7 | 0 | ● | 0 | ● |

TABLE 6

| EXAMPLES | Film | Transferability | Acid Type | Film Surface Properties | | Microbicidal Ability | | | |
|---|---|---|---|---|---|---|---|---|---|
| | | | | Water Spread (mm) | pH | Normal Temperature | | High Temperature, High Humidity | |
| | | | | | | Bacteria Survival Rate (%) | Judge | Bacteria Survival Rate (%) | Judge |
| Example 1 | moth-eye | ○ | TMBA | 31.5 | 3.7 | 0 | ● | 0 | ● |
| Example 2 | moth-eye | ○ | TMBA | 31.0 | 3.8 | 0 | ● | 0 | ● |
| Example 3 | moth-eye | ○ | TMBA | 30.5 | 4.2 | 3.8 | ○ | 7.8 | ○ |
| Example 4 | moth-eye | ○ | TMBA | 30.5 | 4.6 | 15.6 | Δ | 38.5 | Δ |
| Example 5 | moth-eye | ○ | TMBA/DPPA | 31.5 | 4.9 | 20.5 | Δ | 28.8 | Δ |
| Example 6 | moth-eye | ○ | TMBA/DPPA | 32.0 | 4.9 | 21.3 | Δ | 24.5 | Δ |
| Example 7 | moth-eye | ○ | BA | 30.5 | 4.3 | 8.7 | ○ | 8.5 | ○ |
| Example 8 | moth-eye | ○ | BA | 30.0 | 4.6 | 25.5 | Δ | 25.8 | Δ |
| Example 9 | moth-eye | Δ | TMBA | 31.5 | 4.4 | 7.8 | ○ | 8.5 | ○ |
| Example 10 | moth-eye | Δ | succinic acid | 30.5 | 4.1 | 2.5 | ○ | 31.3 | Δ |
| Example 11 | moth-eye | Δ | adipic acid | 30.5 | 4.3 | 4.6 | ○ | 18.5 | Δ |

TABLE 6-continued

| EXAMPLES | Film | Transferability | Acid Type | Film Surface Properties | | Microbicidal Ability | | | |
|---|---|---|---|---|---|---|---|---|---|
| | | | | | | Normal Temperature | | High Temperature, High Humidity | |
| | | | | Water Spread (mm) | pH | Bacteria Survival Rate (%) | Judge | Bacteria Survival Rate (%) | Judge |
| Example 12 | moth-eye | Δ | suberic acid | 30.0 | 4.6 | 5.2 | ○ | 6.4 | ○ |
| Example 13 | moth-eye | Δ | sebacic Acid | 30.0 | 4.7 | 6.4 | ○ | 6.1 | ○ |
| Example 14 | moth-eye | Δ | TMBA/PPA | 31.5 | 3.9 | 0 | ● | 2.3 | ○ |
| Example 15 | moth-eye | ○ | TMBA | 32.0 | 3.5 | 0 | ● | 0 | ● |
| Example 16 | moth-eye | ● | TMBA | 45.5 | 3.9 | 0 | ● | 2.5 | ○ |

TABLE 7

| COMPARATIVE EXAMPLES | Film | Transferability | Acid Type | Film Surface Properties | | Microbicidal Ability | | | |
|---|---|---|---|---|---|---|---|---|---|
| | | | | | | Normal Temperature | | High Temperature, High Humidity | |
| | | | | Water Spread (mm) | pH | Bacteria Survival Rate (%) | Judge | Bacteria Survival Rate (%) | Judge |
| Comparative Example 1 | moth-eye | ○ | not detected | 30.0 | 7.2 | 91.4 | x | 98.7 | x |
| Comparative Example 2 | moth-eye | Δ | dodecanedioic acid | 30.5 | 5.5 | 78.4 | x | 77.4 | x |
| Comparative Example 3 | moth-eye | Δ | acetic acid | 31.5 | 4.1 | 1.3 | ○ | 89.4 | x |
| Comparative Example 4 | moth-eye | Δ | PPA | 31.0 | 4.6 | 89.7 | x | 98.8 | x |
| Comparative Example 5 | moth-eye | ● | TMBA | 8.0 | 6.0 | 74.5 | x | 77.3 | x |
| Comparative Example 6 | moth-eye | Δ | TMBA | 12.5 | 6.6 | 95.5 | x | 89.5 | x |

The sample film of Reference Example shown in TABLE 5 has poor transferability because the synthetic polymer film has a urethane bond. Therefore, the sample film of Reference Example is poor in mass productivity although the microbicidal ability is excellent.

Each of the sample films of Examples and Comparative Examples is excellent in transferability because the synthetic polymer film does not have a urethane bond.

The synthetic polymer films of Examples 1 to 16 were formed using a UV-curable resin composition which contained an acrylic monomer (M280) having an ethylene oxide unit (EO unit). Therefore, the synthetic polymer films of Examples 1 to 16 have appropriate hydrophilicity, and the surface that has the moth-eye structure is a superhydrophilic surface. The synthetic polymer films of Examples 10 to 13 contain ACMO (monofunctional acrylic monomer). This is for the purpose of making the acrylic monomer constituent comparable with the synthetic polymer film of Comparative Example 2 in which ACMO was added for dissolving the dodecanedioic acid. Although ACMO contains a nitrogen element, the nitrogen element is a constituent of a tertiary amine, and its polarity is not strong as compared with primary and secondary amines.

The synthetic polymer film of Comparative Example 6 does not contain an ethylene oxide unit and is therefore poor in hydrophilicity. This can be seen from TABLE 7 showing that the degree of spread of water (area equivalent circle diameter) is small, specifically not more than 20 mm.

Also in Comparative Example 5, the degree of spread of water is small. Comparative Example 5 is different from Example 16 only in the type of the mold releasing agent, and the composition of the other constituents is the same as that of Example 16. It can be seen from this that, when a fluorine-containing mold releasing agent is used, the microbicidal ability deteriorates although the transferability improves. Also, it can be seen that the degree of spread of water is a significant factor in the microbicidal ability. Among the samples which were judged to have a microbicidal ability, the degree of spread of water was the smallest in Reference Example (28.5 mm). It is supposed that the degree of spread of water is preferably at least not less than 20 mm, more preferably not less than 30 mm. On the other hand, in Example 16 in which the silicone-based surfactant was used, the transferability improved while the degree of spread of water increased, and the microbicidal ability was excellent. The mold releasing agent is preferably an agent which is locally present on the surface so that the degree of spread of water can increase and the transferability can improve, such as a silicone-based surfactant.

It can be seen from the comparison between Examples and Comparative Examples that the microbicidal ability has not only a correlation with the degree of spread of water but also a correlation with the pH of the aqueous solution.

First, compare Example 1 with Comparative Example 1. The difference between Example 1 and Comparative Example 1 is only the type of the polymerization initiator. Polymerization initiator 819 used in Example 1 generates 2,4,6-trimethylbenzoic acid (TMBA) by photodecomposition. This was verified by GC-MAS. On the other hand, polymerization initiator OXE02 used in Comparative Example 1 does not generate an acid by photodecomposition. As a result, Comparative Example 1 does not have a microbicidal ability because the pH is 7.2, although the degree of spread of water is 30 mm, which is comparable to the degree of spread of water of Example 1 (31.5 mm).

Polymerization initiator 819 used in Examples 1 to 4 generates TMBA by photodecomposition. Polymerization initiator TPO used in Examples 5 and 6 generates TMBA and diphenyl phosphoric acid (DPPA). Polymerization initiator OXE01 used in Examples 7 and 8 generates benzoic acid (BA). Therefore, the pH of the aqueous solution of the synthetic polymer films of Examples 1 to 8 is not more than 5, and the degree of spread of water is not less than 30 mm, so that the synthetic polymer films of Examples 1 to 8 have an excellent microbicidal ability. Polymerization initiator 819 used in Examples 1 to 4 can generate two TMBA molecules at the maximum per one molecule of the polymerization initiator and is therefore preferred. As seen from the results of Examples 1 to 4, it is preferred that the proportion of the contained polymerization initiator 819 to the entirety of the photocurable resin composition is not less than 2 mass %.

In Examples 9 to 14, polymerization initiator OXE02 which does not generate an acid was used, and in addition, an organic carboxylic acid was added. Each of Examples 9 to 14 has an excellent microbicidal ability. As for the solubility of the organic carboxylic acid in water, in each of Examples 9 to 14, the amount of water required for dissolving 1 g of the organic carboxylic acid is not less than 10 mL and less than 10000 mL (solubility index: 3 to 6). The amount of water is preferably not less than 100 mL, more preferably not less than 200 mL, and is preferably less than 2000 mL. If the solubility of the organic carboxylic acid in water is excessively high, the microbicidal effect in a high-temperature, high-humidity environment decreases earlier.

Example 14 is equal to the composition of Example 9 except the addition of phenyl phosphoric acid (PPA) and has a better microbicidal ability than Example 9. This is probably because the addition of PPA, which is a stronger acid than TMBA, suppressed dissociation of TMBA and, as a result, TMBA was taken into a cell so that a microbicidal activity was exhibited.

As seen from the foregoing, the fast spreading of water dropped onto the surface of the synthetic polymer film advantageously affects the microbicidal ability. In this process, due to an acid extracted into water, the pH of the aqueous solution (water drop) decreases (becomes acidified) within a relatively short time period. A microbicidal activity which is attributed to this decrease of the pH effectively works. At the lapse of 5 minutes, the pH is preferably not more than 5. If the pH is not more than 5, a microbicidal activity which is attributed to taking of an undissociated organic carboxylic acid into a cell effectively works. If an acid stronger than the organic carboxylic acid, such as phosphoric acid or sulfonic acid, is contained, dissociation of the organic carboxylic acid is further suppressed. Thus, such an acid is preferred to be contained.

The solubility of dodecanedioic acid of Comparative Example 2 in water is very low (solubility index 7). Therefore, Comparative Example 2 does not exhibit a microbicidal effect which is attributed to the organic carboxylic acid. On the other hand, the acetic acid of Comparative Example 3 and the phenyl phosphoric acid of Comparative Example 4 have extremely high solubility in water (solubility index 1). Therefore, Comparative Example 3 and Comparative Example 4 have a low microbicidal ability and, particularly, have a low microbicidal ability in a high-temperature, high-humidity environment.

Examples of the organic carboxylic acid suitably used in the synthetic polymer film of an embodiment of the present invention are as follows:

fatty acids, such as pentanoic acid, hexanoic acid, heptanoic acid, octanoic acid;

aromatic carboxylic acids, such as benzoic acid, 2,4,6-trimethylbenzoic acid, salicylic acid; and diprotic acids, such as succinic acid, fumaric acid, adipic acid, pimelic acid, suberic acid, azelaic acid, sebacic acid, o-phthalic acid.

From the viewpoint of solubility and safety, suberic acid, sebacic acid and 2,4,6-trimethylbenzoic acid are preferably used. The amount of water required for dissolving 1 g of these organic carboxylic acids is not less than 200 mL and less than 2000 mL.

The organic carboxylic acid only needs to be contained in the synthetic polymer film. The photocurable resin may generate an organic carboxylic acid by photodecomposition. The compound which generates an organic carboxylic acid by photodecomposition may be an initiator or may be a photoacid generator which does not function as the initiator as described above. When a radically-polymerizable photocurable resin is used as the photocurable resin, a photoacid generator which generates an organic carboxylic acid without generating a radical can be used. The compound which generates an organic carboxylic acid by photodecomposition is, advantageously, unlikely to deteriorate the transferability. Also, advantageously, the compound can simultaneously generate the organic carboxylic acid and another water-soluble organic acid (an acid stronger than carboxylic acid).

The photoacid generator which generates an organic carboxylic acid may be selected from known photoacid generators. Examples of the photoacid generator include naphthalene diazides such as 6-diazo-5,6-dihydro-5-oxo-1-naphthalene sulfonic acid, benzophenones such as 2,3,4-trihydroxybenzophenone, and polyphenols such as 4-{4-[1, 1-bis(4-hydroxyphenyl)ethyl]-α,α-dimethyl benzyl} phenol.

As described above, the resin composition used in Example 15 was equal to the UV-curable resin composition of Example 3 except the addition of water. As seen from the results of TABLE 6, Example 15 has a better microbicidal ability than Example 3. By adding water to the UV-curable resin composition used in Example 3, the organic carboxylic acid was more readily extracted so that the pH decreased, and the hydrophilicity of the surface increased so that the degree of spread of water increased.

When water is added to and mixed in the UV-curable resin composition, the stability decreases. Therefore, the addition of water is preferably carried out immediately before the light irradiation step in the above-described manufacturing method. The amount of water is preferably not less than 1 mass % and not more than 10 mass % with respect to the entirety of the photocurable resin composition. If the amount of water is less than 1 mass %, the effect of the addition cannot be achieved sometimes. If the amount of water is more than 10 mass %, a homogeneous composition cannot be obtained sometimes.

The sample films of Examples 17 to 19 were produced with different types of polymerization initiators contained in the UV-curable resin. The compositions of Examples 17 to 19 are shown in TABLE 8. The sample films of Examples 17 to 19 were produced by the same method as that previously described for Examples 1 to 16 and evaluated as to the microbicidal ability, the transferability and the film surface properties by the same method as that previously described for Examples 1 to 16. The evaluation results of the sample films of Examples 17 to 19 as to the microbicidal ability, the transferability and the film surface properties are shown in TABLE 9.

erization initiator 819 can generate two TMBA molecules at the maximum per one molecule of the polymerization initiator. Therefore, it is estimated that Example 19 which contains both polymerization initiators 819 and TPO has an excellent microbicidal ability. For example, it is preferred that the proportion of the contained polymerization initiator 819 to the entirety of the photocurable resin composition is not less than 1 mass % and the proportion of the contained polymerization initiator TPO to the entirety of the photocurable resin composition is not less than 1 mass %.

In the foregoing, a synthetic polymer film which has a moth-eye structure over the surface has been described, although an embodiment of the present invention is not limited to this example. A synthetic polymer film of an embodiment of the present invention may have a plurality of

TABLE 8

| EXAMPLES | Acrylic Monomer | | | Initiator | | | | Mold Releasing Agent |
|---|---|---|---|---|---|---|---|---|
| | M280 | M282 | ACMO | 819 | TPO | OXE01 | OXE02 | SAG003 |
| Example 17 | 48.8% | 48.8% | | 2.0% | | | | 0.5% |
| Example 18 | 48.8% | 48.8% | | | 2.0% | | | 0.5% |
| Example 19 | 48.8% | 48.8% | | 1.0% | 1.0% | | | 0.5% |

TABLE 9

| EXAMPLES | Film | Transferability | Acid Type | Film Surface Properties | | Microbicidal Ability Normal Temperature | | |
|---|---|---|---|---|---|---|---|---|
| | | | | Water Spread (mm) | pH | Bacteria Survival Rate (%) | Judge | |
| Example 17 | moth-eye | ● | TMBA | 32.5 | 4.1 | 4.7 | ○ | |
| Example 18 | moth-eye | ● | TMBA/DPPA | 32.0 | 4.9 | 38.2 | Δ | |
| Example 19 | moth-eye | ● | TMBA/DPPA | 33 | 4.1 | 0 | ● | |

Examples 17 to 19 are different from one another only in the type of the polymerization initiator. In Example 17, 819 was used as the polymerization initiator. In Example 18, TPO was used as the polymerization initiator. In Example 19, 819 and TPO were used as the polymerization initiator. In each of Examples 17 to 19, the proportion of the contained polymerization initiator to the entirety of the photocurable resin composition was 2 mass %.

In each of the synthetic polymer films of Examples 17 to 19, the pH of the aqueous solution at the lapse of 5 minutes was not more than 5 and the degree of spread of water was not less than 20 mm. Thus, the synthetic polymer films of Examples 17 to 19 have an excellent microbicidal ability. None of the synthetic polymer films of Examples 17 to 19 has a urethane bond. Thus, the synthetic polymer films of Examples 17 to 19 are excellent in transferability. As seen from the results of TABLE 9, Example 19 has a better microbicidal ability than Example 17. It is estimated that since Example 19 further contained DPPA which is an stronger acid than TMBA in addition to TMBA, dissociation of TMBA was suppressed, and Example 19 exhibited an excellent microbicidal ability. Although Example 18 also contains TMBA and DPPA, Example 19 has a better microbicidal ability than Example 18. Polymerization initiator TPO can generate one TMBA molecule at the maximum per one molecule of the polymerization initiator, while polymraised portions over the surface, and the two-dimensional size of the plurality of raised portions may be not less than 500 nm when viewed in the normal direction of the synthetic polymer film. The synthetic polymer film having such a structure can also achieve the same effects as those achieved by the synthetic polymer film which has the moth-eye structure over the surface. The surface structure is not limited to the raised portions but may be recessed portions. A synthetic polymer film of an embodiment of the present invention may have a plurality of raised or recessed portions over the surface, and the two-dimensional size of the plurality of raised or recessed portions may be not less than 500 nm when viewed in the normal direction of the synthetic polymer film.

The sample films of Examples 20 and 21 were produced using UV-curable resins whose compositions are shown in TABLE 10. The compositions of Examples 20 and 21 are shown in TABLE 10. The sample films of Examples 20 and 21 are different from the film 50A shown in FIG. 1A in the surface structure of the synthetic polymer film 34A. To produce the synthetic polymer films of the sample films of Examples 20 and 21, mold samples which are described below were prepared. The mold sample of Example 20 was obtained by forming an aluminum alloy layer (thickness: 0.6 μm) on a glass substrate (5 cm×10 cm) and forming a high-purity aluminum layer (thickness: 0.4 μm, aluminum purity: not less than 99.99 mass %) on the aluminum alloy layer. The aluminum alloy layer contained aluminum (Al) and titanium (Ti). The content of Ti in the aluminum alloy layer was 0.5 mass %. The mold sample of Example 21 was obtained by forming a high-purity aluminum layer (thickness: 4 μm, aluminum purity: not less than 99.99 mass %) on a glass substrate (5 cm×10 cm). Except that the thus-obtained mold samples were used, the sample films of Examples 20 and 21 were produced by the same method as that previously described for Examples 1 to 16.

As disclosed in WO 2016/084745 of the present applicant, by adjusting the composition and/or the film formation conditions (e.g., the thickness of the aluminum alloy layer) of the aluminum alloy layer which contains Al and Ti, the crystal grain diameter of a plurality of crystal grains which are present at the surface of the aluminum alloy layer can be adjusted. Also, as disclosed in WO 2011/052652 of the present applicant, by adjusting the film formation conditions of an aluminum film which is to be formed on a substrate (e.g., glass substrate), the crystal grain diameter of a plurality of crystal grains which are present at the surface of the aluminum film can be adjusted. When a porous alumina layer obtained by alternately performing anodization and etching on the thus-obtained aluminum alloy layer or aluminum film is used as the mold, an antireflection film which can perform an antiglare function can be formed. Note that, however, the mold samples for formation of the sample films of Examples 20 and 21 were obtained without performing anodization or etching on a high-purity aluminum layer. The entire disclosures of WO 2016/084745 and WO 2011/052652 are incorporated by reference in this specification.

Figure 8A:
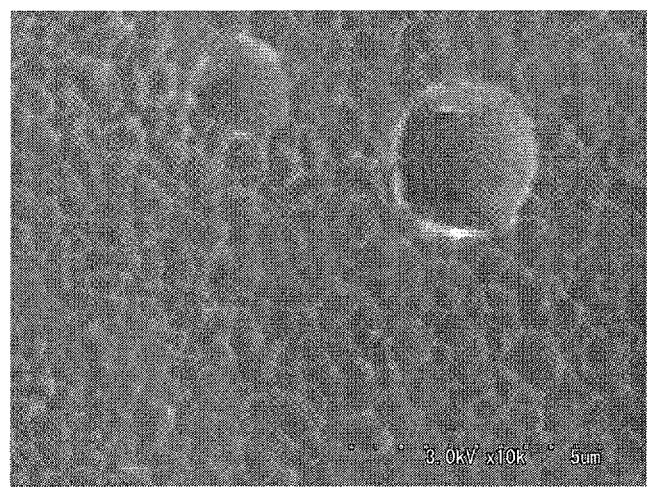
FIG. 8A shows a SEM image of a surface of a mold sample used in production of a sample film of Example 20.
Figure 8B:
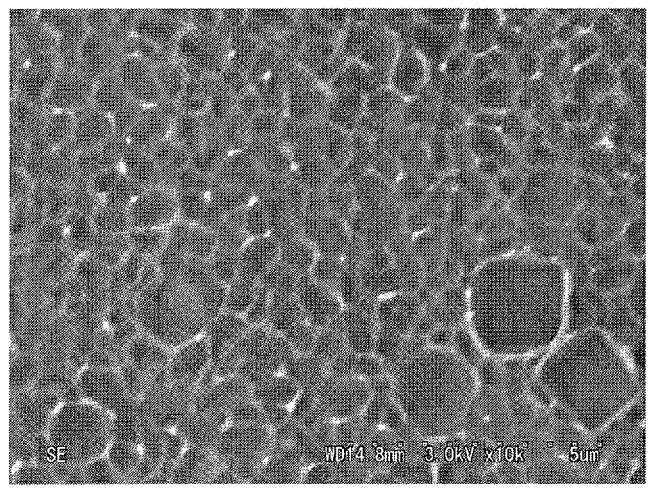
FIG. 8B shows a SEM image of a surface of a mold sample used in production of a sample film of Example 21.

FIG. 8A shows a SEM image of a surface of the mold sample of Example 20. FIG. 8B shows a SEM image of a surface of the mold sample of Example 21. The two-dimensional size of a plurality of crystal grains was determined from the SEM images as described in the following paragraphs.

As shown in FIG. 8A and FIG. 8B, a region of 9 μm×12 μm was selected from the surface SEM images (×10000) of the mold samples. From the selected region, 20 crystal grains were arbitrarily selected in that region, exclusive of irregularly-large crystal grains as compared with the majority of the crystal grains (also referred to as "abnormal grains"). The area equivalent circle diameters of the selected crystal grains were averaged. For example, grains with particularly large grain diameters, which are seen at the upper right area and the upper central area in the SEM image of FIG. 8A, are abnormal grains. The mold samples of Examples 20 and 21 have raised portions corresponding to the crystal grains and recessed portions at the grain boundaries.

TABLE 10

| EXAMPLES | Acrylic Monomer | | | Initiator | | | | Mold Releasing Agent |
| --- | --- | --- | --- | --- | --- | --- | --- | --- |
| | M280 | M282 | ACMO | 819 | TPO | OXE01 | OXE02 | SAG003 |
| Example 20 | 97.1% | | | | | 1.9% | | 1.0% |
| Example 21 | 46.6% | 46.6% | 2.9% | 2.9% | | | | 1.0% |

The sample films of Examples 20 and 21 each has a shape obtained by inverting the surface shape of the mold sample. The "two-dimensional size" of Examples 20 and 21 shown in TABLE 11 refers to the two-dimensional size of a plurality of raised portions at the surface of the mold samples of Examples 20 and 21.

The sample films of Examples 20 and 21 were evaluated as to the microbicidal ability, the transferability and the film surface properties by the same method as that previously described for Examples 1 to 16. The evaluation results of the sample films of Examples 20 and 21 as to the microbicidal ability, the transferability and the film surface properties are shown in TABLE 11.

TABLE 11

| EXAMPLES | Two-dimensional Size (μm) | Transferability | Acid Type | Film Surface Properties Water Spread (mm) | pH | Microbicidal Ability Normal Temperature Bacteria Survival Rate (%) | Judge |
| --- | --- | --- | --- | --- | --- | --- | --- |
| Example 20 | 0.62 | ● | BA | 22.5 | 4.7 | 35.4 | Δ |
| Example 21 | 0.74 | ● | TMBA | 20.5 | 4.1 | 1.1 | ○ |

In each of the synthetic polymer films of Examples 20 and 21, the pH of the aqueous solution at the lapse of 5 minutes was not more than 5 and the degree of spread of water was not less than 20 mm. Thus, the synthetic polymer films of Examples 20 and 21 have an excellent microbicidal ability. None of the synthetic polymer films of Examples 20 and 21 has a urethane bond. Thus, the synthetic polymer films of Examples 20 and 21 are excellent in transferability.

As seen from the results of Examples 20 and 21, a synthetic polymer film of an embodiment of the present invention has an excellent microbicidal ability so long as a plurality of recessed portions at the surface of the synthetic polymer film are in the range of, for example, not less than 500 nm and not more than 1 μm. That is, it is estimated that so long as the pH of the aqueous solution at the lapse of 5 minutes is not more than 5 and the degree of spread of water is not less than 20 mm, the synthetic polymer film has an excellent microbicidal ability irrespective of whether the structure at the surface of the synthetic polymer film is a plurality of raised portions or a plurality of recessed portions. In this case, it is estimated that the two-dimensional size of the plurality of raised portions or the plurality of recessed portions only needs to be in the range of more than 20 nm and not more than 1 μm.

The mold samples of Examples 20 and 21 can be obtained only by forming crystal grains of a desired shape (e.g., the average grain diameter is not less than 500 nm and not more than 1 μm). That is, it is not necessary to perform anodization as in formation of the moth-eye mold. Thus, the mold samples of Examples 20 and 21 can be manufactured at a low cost. Also, advantageously, the mold samples of Examples 20 and 21 are excellent in transferability.

Herein, the UV-curable resin has been described, although a resin which can be cured with visible light can be used. Note that, however, the UV-curable resin is preferred because it can be stored and handled easily.

A synthetic polymer film of an embodiment of the present invention is capable of sterilizing water adhered to the surface of the film within a short time period. Therefore, by placing the synthetic polymer film on the inner surface of a space of a hand dryer into which a hand is to be inserted, infection can be suppressed and prevented.

A synthetic polymer film according to an embodiment of the present invention is suitably applicable to uses which require sterilization of water within a short time period.

While the present invention has been described with respect to exemplary embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

This application is based on Japanese Patent Applications No. 2017-185204 filed on Sep. 26, 2017 and No. 2017-226887 filed on Nov. 27, 2017, the entire contents of which are hereby incorporated by reference.

What is claimed is:

1. A synthetic polymer film whose surface comprises a plurality of raised or recessed portions,
wherein the synthetic polymer film has a crosslink structure, and the crosslink structure does not contain any nitrogen element that is a constituent of a urethane bond,
the synthetic polymer film contains an organic carboxylic acid, and an amount of water required for dissolving 1 g of the organic carboxylic acid is equal to or greater than 10 mL and less than 10000 mL,
at the lapse of 5 minutes since placing a 200 μL drop of water on the surface of the synthetic polymer film, a pH of an aqueous solution is not more than 5, the aqueous solution containing the water and the organic carboxylic acid extracted from the synthetic polymer film, and an area equivalent circle diameter of the aqueous solution is not less than 20 mm,
the synthetic polymer film is formed from a photocurable resin containing a photopolymerization initiator,
the organic carboxylic acid is contained in the photocurable resin or is generated by photodecomposition of a compound that is contained in the photocurable resin but does not function as an initiator,
when viewed in a normal direction of the synthetic polymer film, a two-dimensional size of the plurality of raised or recessed portions is in the range of not less than 500 nm and not more than 1 μm,
the plurality of raised or recessed portions is formed by directly transferring a shape of an outermost surface of a mold to the synthetic polymer film,
the mold has an aluminum layer and the outermost surface of the mold is a surface of the aluminum layer that has a plurality of crystal grains, and
the shape of the outermost surface of the mold includes a surface shape of the plurality of crystal grains.

2. The synthetic polymer film of claim 1, wherein the synthetic polymer film further contains an acid stronger than the organic carboxylic acid.

3. The synthetic polymer film of claim 1, wherein the organic carboxylic acid is 2,4,6-trimethylbenzoic acid, suberic acid or sebacic acid.

4. The synthetic polymer film of claim 1, wherein the synthetic polymer film further contains an organic carboxylic acid generated by photodecomposition of the photopolymerization initiator.

5. The synthetic polymer film of claim 4, wherein the photopolymerization initiator contains bis(2,4,6-trimethyl-benzoyl)-phenylphosphine oxide.

6. The synthetic polymer film of claim 5, wherein the photopolymerization initiator further contains diphenyl (2,4,6-trimethylbenzoyl) phosphine oxide.

7. The synthetic polymer film of claim 1, wherein the crosslink structure contains an ethylene oxide unit.

8. The synthetic polymer film of claim 1, wherein a surface shape of the outermost surface of the mold defines the plurality of crystal grains.

9. A method for sterilizing a liquid including water by bringing the liquid into contact with the surface of the synthetic polymer film as set forth in claim 1.

* * * * *